United States Patent
Koch et al.

(10) Patent No.: US 9,603,647 B2
(45) Date of Patent: Mar. 28, 2017

(54) ORTHOGNATHIC BENDING PLIERS

(71) Applicant: DePuy Synthes Products, Inc., Raynham, MA (US)

(72) Inventors: Roger Koch, Oberdorf (CH); Robert J. Schoutens, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/989,598

(22) Filed: Jan. 6, 2016

(65) Prior Publication Data

US 2016/0113698 A1    Apr. 28, 2016

Related U.S. Application Data

(62) Division of application No. 13/645,275, filed on Oct. 4, 2012, now Pat. No. 9,254,158.

(51) Int. Cl.
  *A61B 17/58*    (2006.01)
  *A61B 17/88*    (2006.01)
  *A61B 17/80*    (2006.01)

(52) U.S. Cl.
  CPC ...... *A61B 17/8863* (2013.01); *A61B 17/8071* (2013.01); *A61B 17/8085* (2013.01); *A61B 17/8861* (2013.01)

(58) Field of Classification Search
  CPC ............................... A61B 17/70; A61B 17/808
  USPC ..... 81/418–426.5, 421–424, 424.5; 606/101; 72/216, 224, 225, 226, 232, 234
  See application file for complete search history.

(56) References Cited

U.S. PATENT DOCUMENTS

| | | | | |
|---|---|---|---|---|
| 3,747,648 A | * | 7/1973 | Bauer | B21F 1/02 |
| | | | | 140/147 |
| 4,770,070 A | * | 9/1988 | Sowers | B25B 7/00 |
| | | | | 81/418 |
| 6,000,686 A | | 12/1999 | Yates | |
| 6,220,126 B1 | | 4/2001 | Domenge | |
| 7,662,155 B2 | | 2/2010 | Metzger et al. | |
| 2006/0259072 A1 | | 11/2006 | DiEmidio | |
| 2009/0222020 A1 | | 9/2009 | Schmuck et al. | |

FOREIGN PATENT DOCUMENTS

| | | |
|---|---|---|
| CH | 696797 A5 | 12/2007 |
| DE | 2028332 A1 | 12/1971 |
| DE | 10224005 A1 | 12/2003 |
| DE | 10301692 A1 | 8/2004 |
| DE | 102005029165 A1 | 1/2007 |

(Continued)

OTHER PUBLICATIONS

International Patent Application No. PCT/US2012/058759: International Search Report dated May 10, 2013, 8 pages.

(Continued)

*Primary Examiner* — Anu Ramana
(74) *Attorney, Agent, or Firm* — Baker & Hostetler LLP

(57) ABSTRACT

A bending tool can be configured to bend an orthopedic implant and includes a first jaw assembly and a second jaw assembly. The first jaw assembly includes a first base and a first adjustment member that is movably coupled to the first base. The second jaw assembly is movably coupled to the second jaw assembly. The second jaw assembly includes a second base and a second adjustment member that is movably coupled to the second base.

20 Claims, 15 Drawing Sheets

(56) References Cited

FOREIGN PATENT DOCUMENTS

| | | |
|---|---|---|
| EP | 0868978 A1 | 10/1998 |
| EP | 2030596 A1 | 3/2009 |
| EP | 2204130 A1 | 7/2010 |
| JP | 04-047816 | 4/1992 |
| JP | 09-508835 | 9/1997 |
| WO | WO 2006/047581 A2 | 5/2006 |

OTHER PUBLICATIONS

Medartis.RTM., "Orbital Planting System OPS 1.5", Product Information, www.medartis.com/products/modus/midface, accessed Jan. 2012, 12 pages.

English translation of Office Action issued on Aug. 30, 2016 in Japanese application 2015-535618, 4 pages.

* cited by examiner

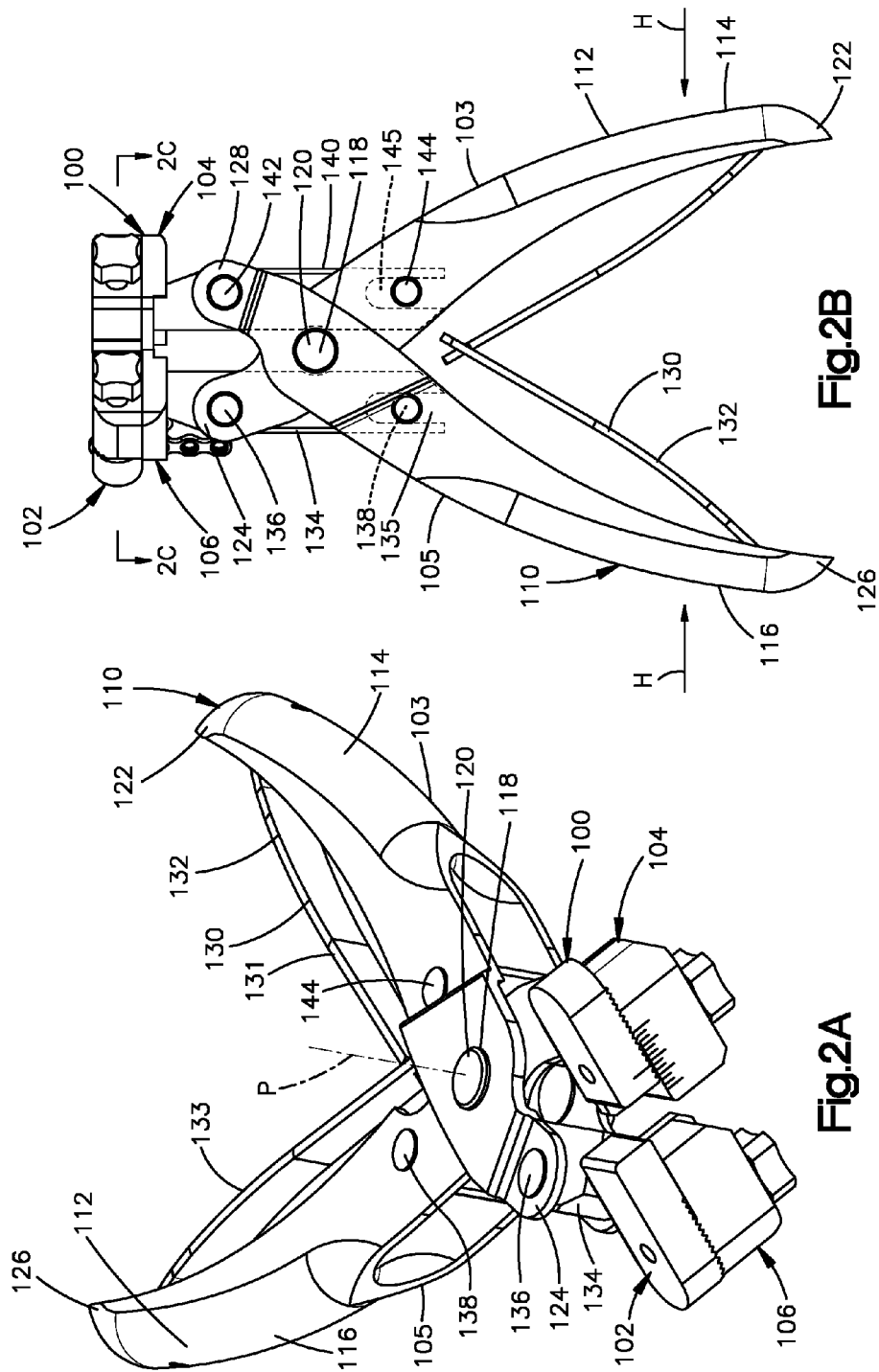

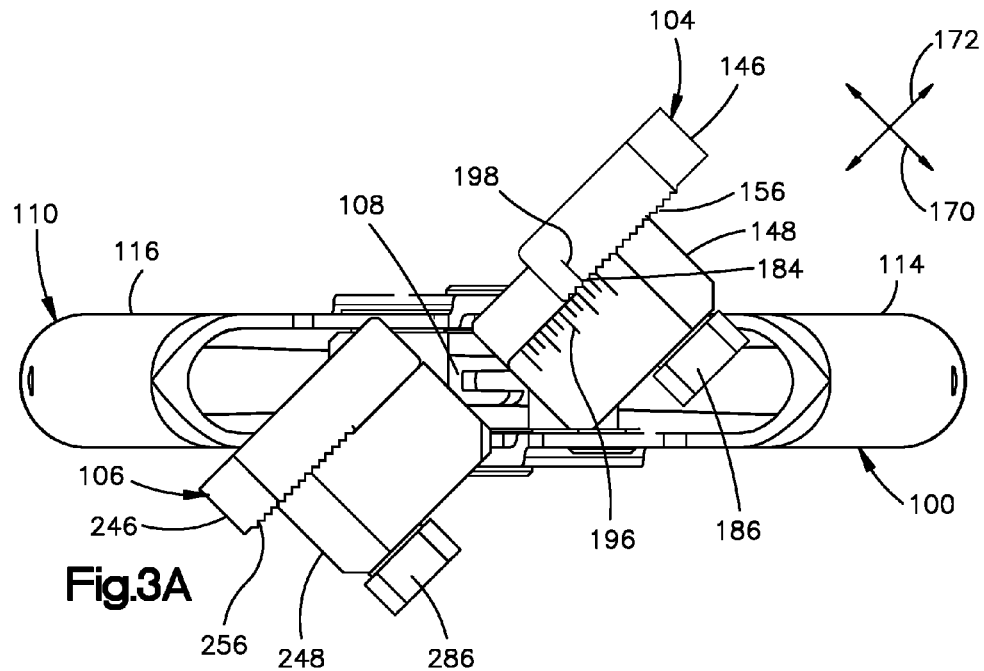
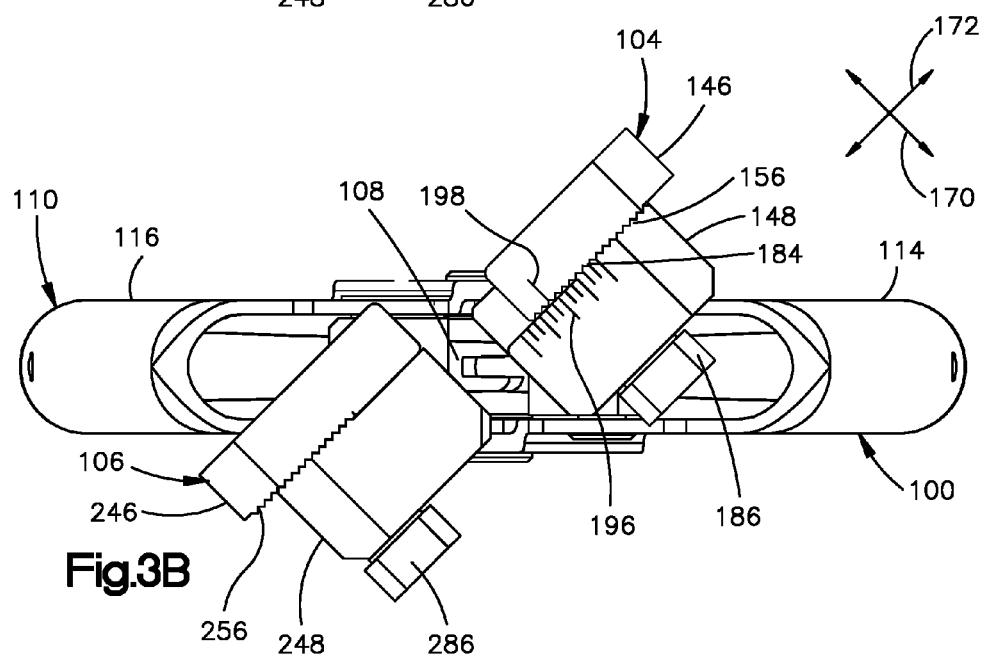

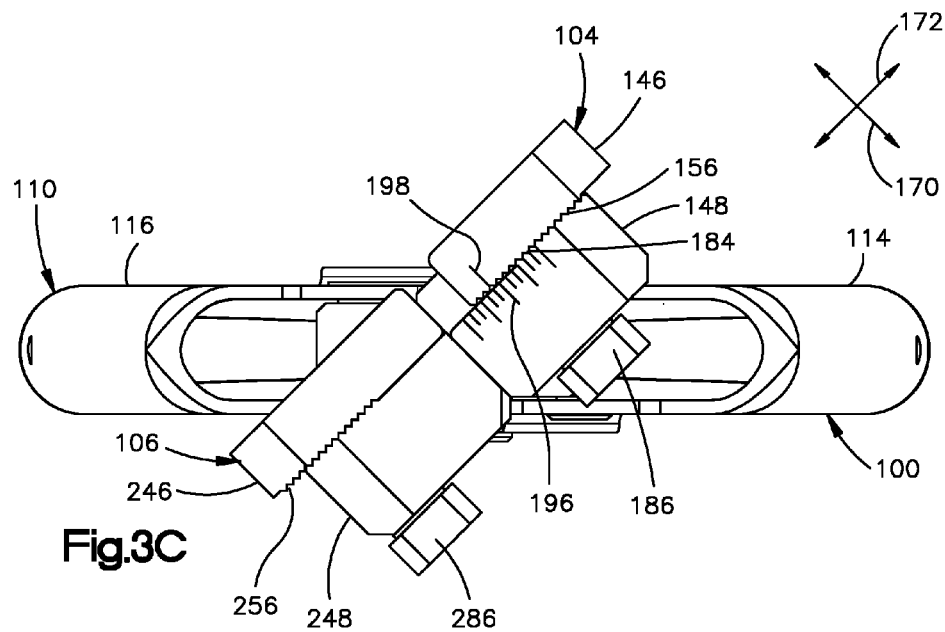
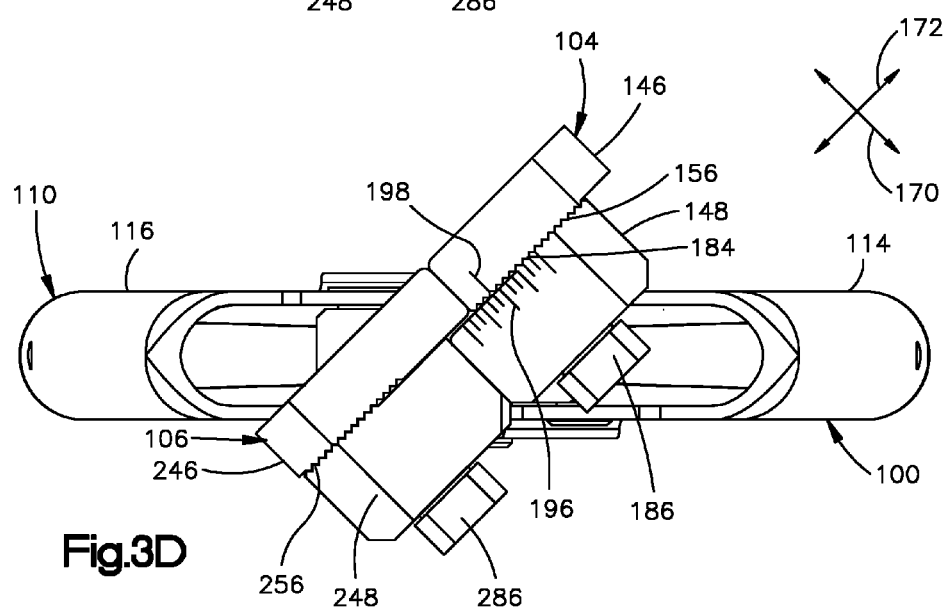

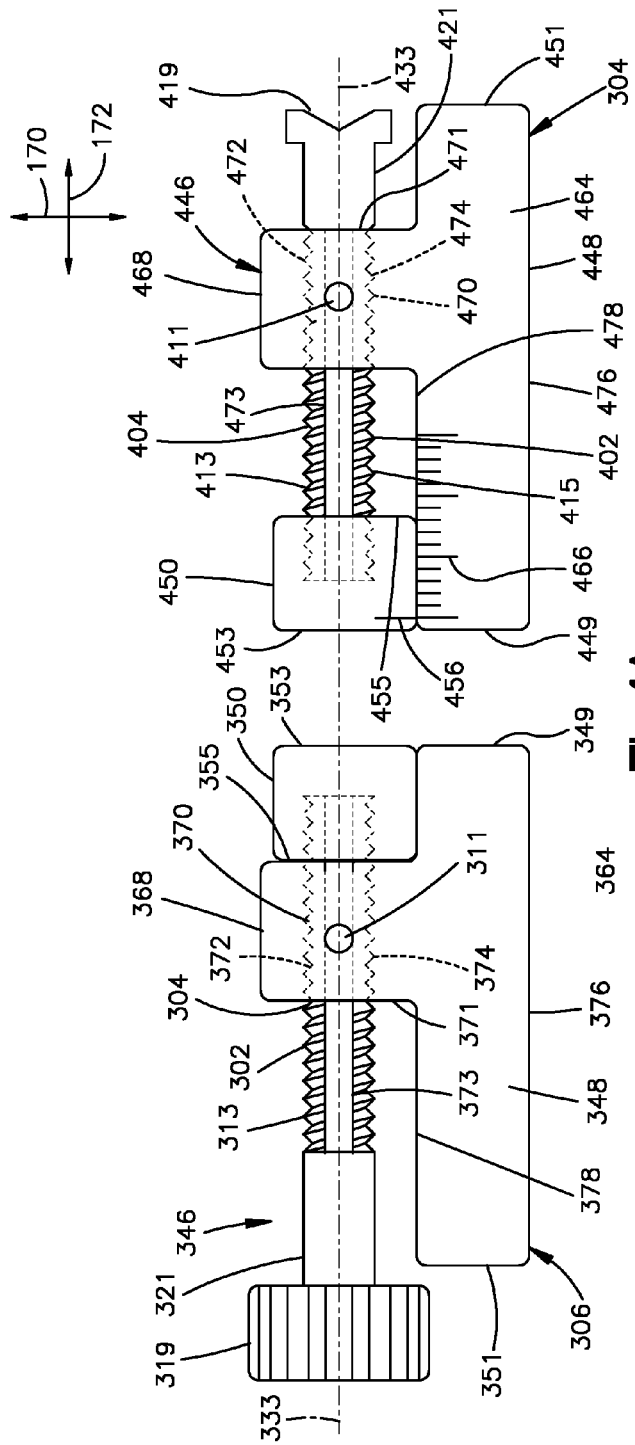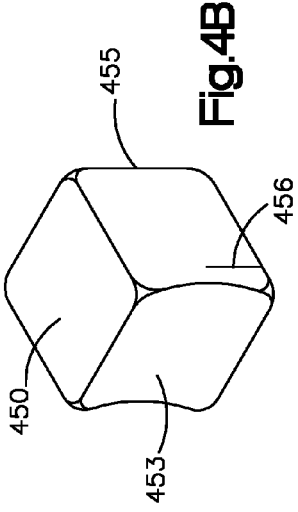
Fig.4A
Fig.4B

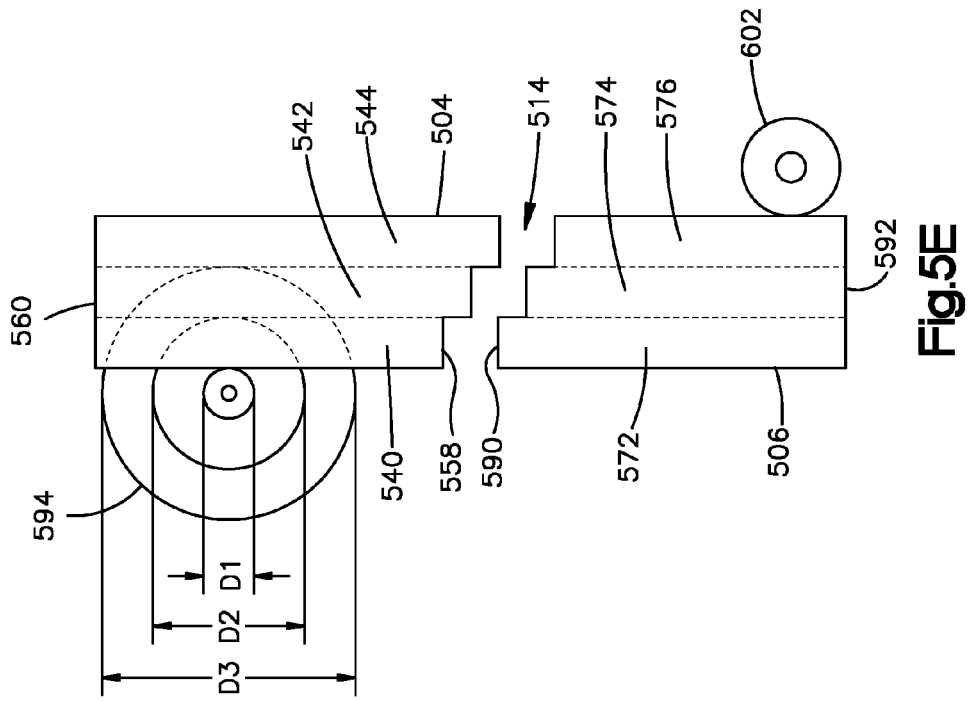
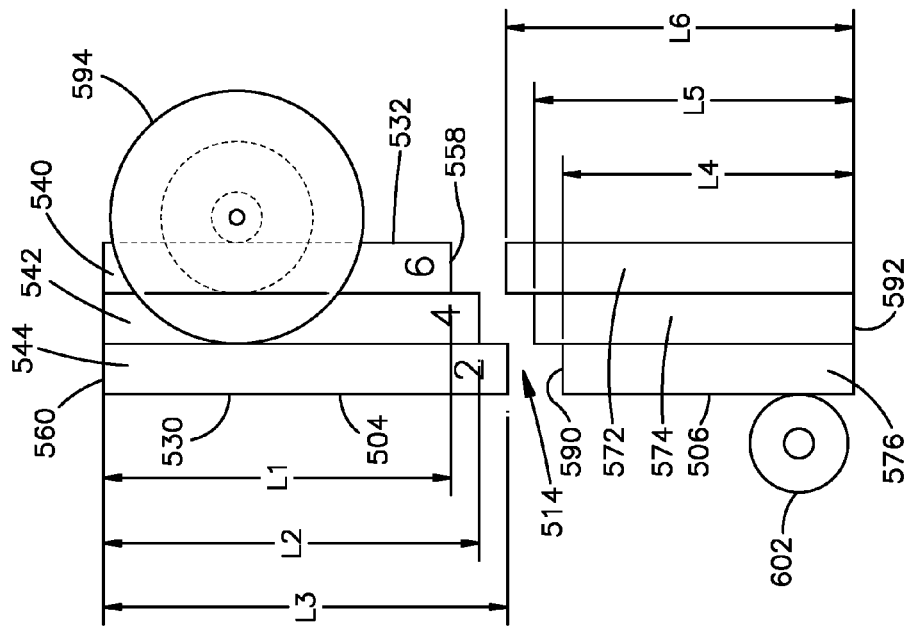
Fig.5E
Fig.5D

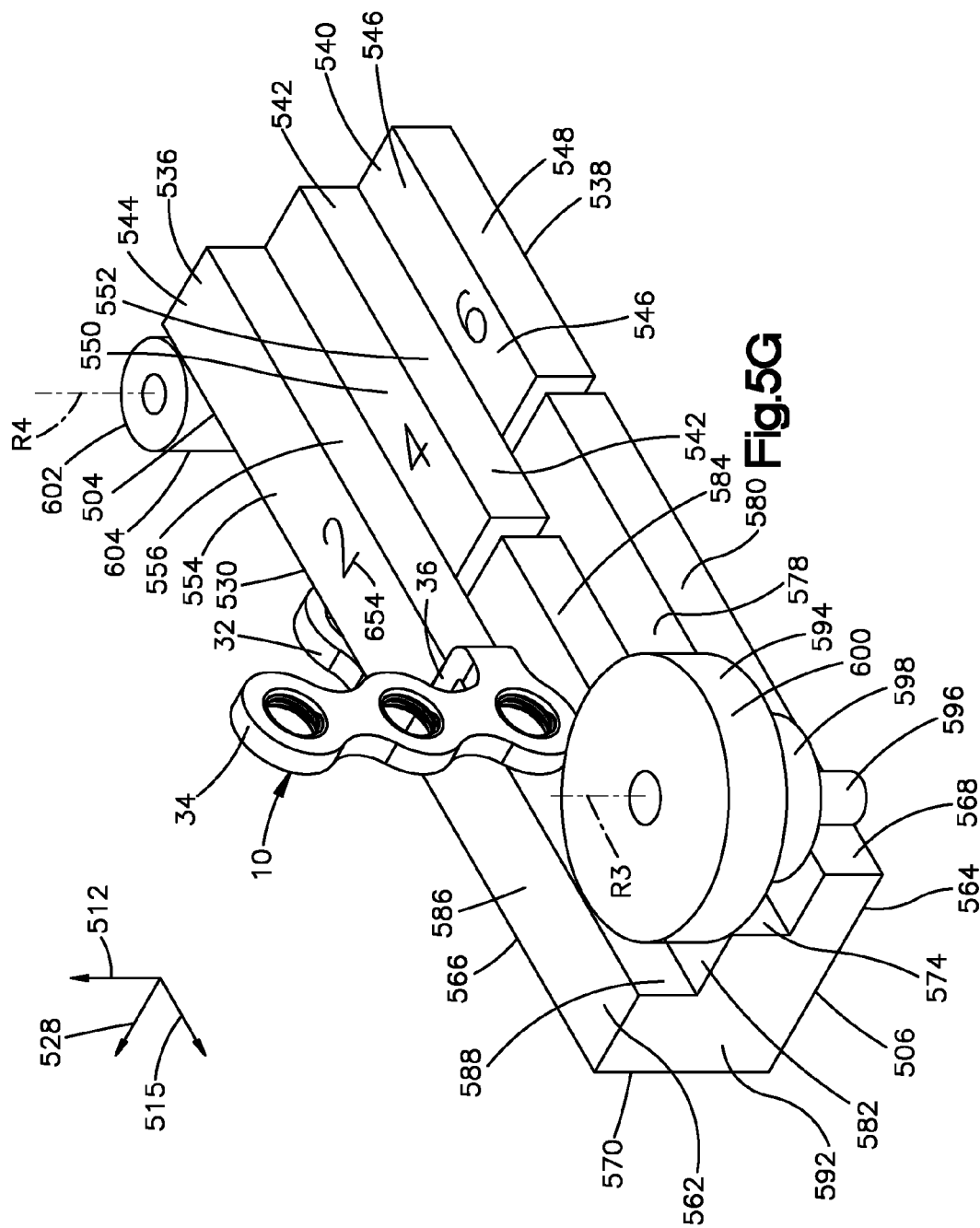

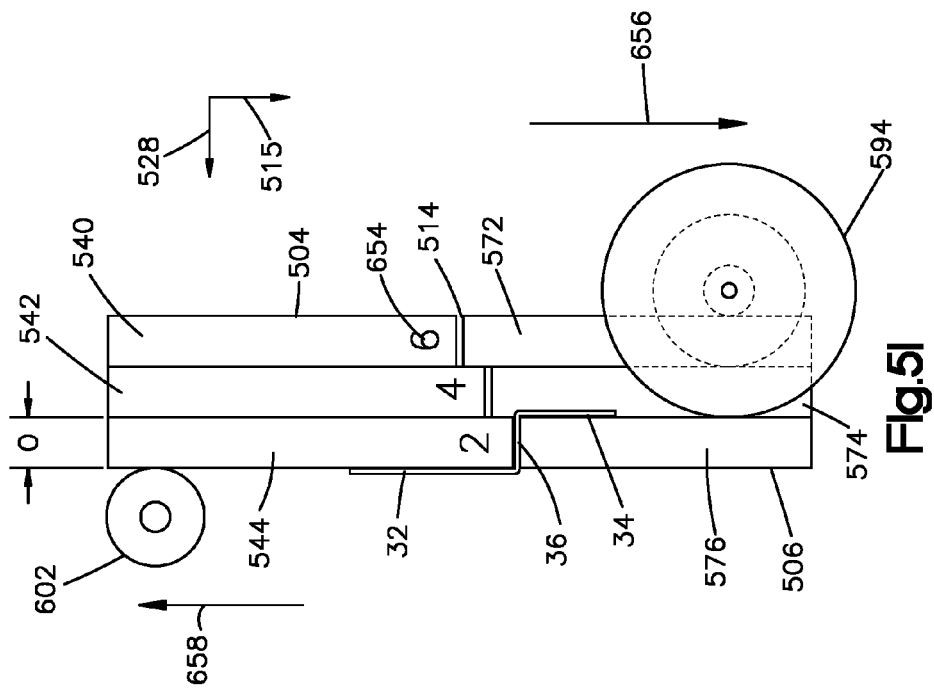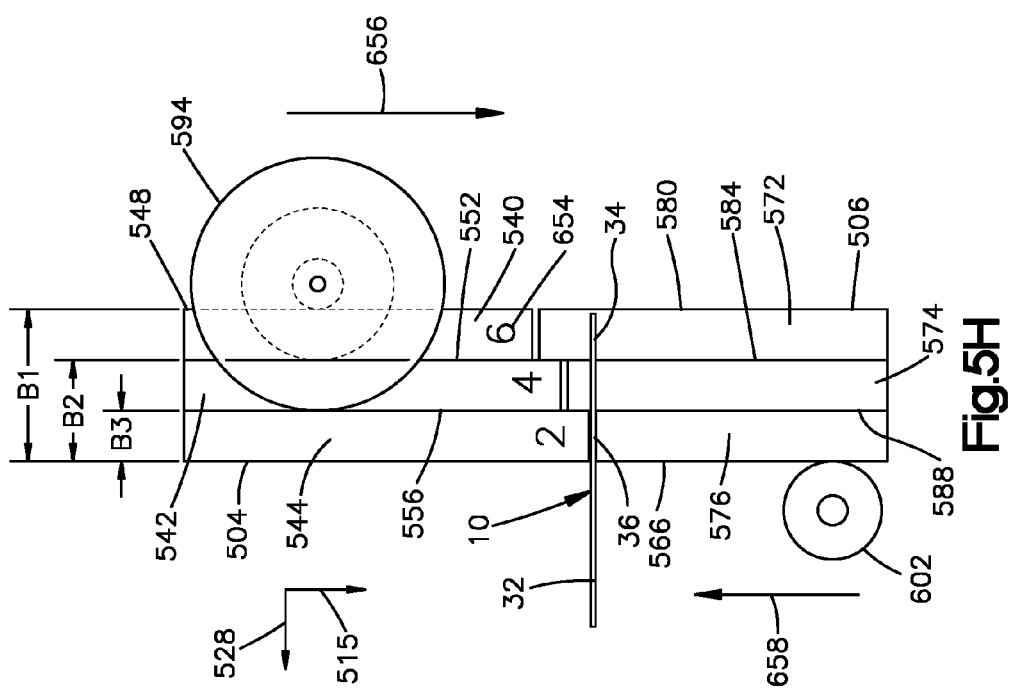

ORTHOGNATHIC BENDING PLIERS

CROSS REFERENCE TO RELATED APPLICATIONS

This application is a divisional of U.S. patent application Ser. No. 13/645,275, filed on Oct. 4, 2012, the disclosure of which is hereby incorporated by reference as if set forth in its entirety herein.

TECHNICAL FIELD

The present disclosure relates to tools and methods for manipulating orthopedic implants, and more particularly, to tools and methods for bending orthognathic plates.

BACKGROUND

Craniofacial surgery can be used to correct a number of conditions of the jaw and face related to structure, growth, sleep apnea, correcting malocclusion problems caused by skeletal disharmonies or other orthodontic problems that cannot be easily treated with braces. During craniofacial surgery, an osteotomy is often performed in which the bones can be cut, realigned, and held in place with either screws or plates and screws. Several craniofacial surgical procedures have been developed over the years. For example, a surgical procedure known as maxillary advancement can be used to correct conditions of the jaw and face. Maxillary advancement involves repositioning the maxilla bone of a patient so that it properly aligns with the mandible. Specifically, maxillary advancement may include the steps of performing a "Lefort I" osteotomy (resection of a maxilla from a remaining portion of a skull); moving the maxilla forward (or anteriorly); and reattaching the maxilla to the remaining portion of the skull using a bone plate and screws until the bone segments grow together and consolidate. In addition, an orthopedic implant may be implanted over the craniofacial defect, such as a fracture, to fix the position of bone segments separated by such defect. Given that the craniofacial anatomies vary, it is difficult to manufacture an orthopedic implant suitable for all anatomical shapes and sizes. Instead, bone plates can be designed to be cut and shaped to conform to a patient's anatomy on a case-by-case basis. The aim of this kind of surgery is to reconstruct the bone anatomy and restore its function. Thus, there is a need for instruments, tools, and methods capable of bending a bone plate.

SUMMARY

The present disclosure relates to tools, systems and methods for bending an orthopedic implant such as a bone plate. The bending tool can be configured to bend an orthopedic implant that includes a first implant portion and a second implant portion. In an embodiment, the bending tool may include a first jaw assembly and a second jaw assembly that is movably coupled to the first jaw assembly. The first jaw assembly includes a first jaw that defines a first engagement surface. The second jaw assembly can be movably coupled to the first jaw assembly and includes a second jaw. The second jaw includes a base and an adjustment member that defines a second engagement surface. The adjustment member can be movably coupled to the base such that the second engagement surface is movable with respect to the first engagement surface so as to at least partially define a gap between the first and second engagement surfaces. The gap has a variable adjustment distance defined from the second engagement surface to the first engagement surface along a lateral direction. In operation, moving the first and second jaw assemblies relative to each other causes at least one of the first and second jaws to move in at least a first lateral direction that decreases the adjustment distance and causes the first and second jaws to apply a force to a portion of the orthopedic implant that is disposed in the gap, thereby bending the orthopedic implant such that the first implant portion is offset relative to the second implant portion by a predetermined offset distance that is at least partially defined by the adjustment distance.

The offset distance may be defined by a difference between the adjustment distance and a thickness of the portion of the orthopedic implant along the lateral direction. The adjustment member can be configured to translate relative to the base. The offset distance may be a first offset distance of a plurality of offset distances. The base may include a plurality of base markings. Each base marking correspond to one of the plurality of offset distances. The adjustment member includes an adjustment marking. The adjustment marking can be configured to be substantially aligned with one of the plurality of base markings such that the first implant portion can be bent relative to the second implant portion by one of the predetermined offset distances.

The adjustment member can be configured to move incrementally relative to the base. The adjustment member may include an adjustment body and adjustment teeth that protrude from the adjustment body. The base may include a base body and base teeth that protrude from the base body. The base teeth can be configured to mate with the adjustment teeth such that the adjustment member is configured to move incrementally relative to the base.

The first jaw may include a first adjustment member and a first base that is movably coupled to the first base. The first adjustment member can be configured to translate relative to the first base. The first adjustment member can be configured to move incrementally relative to the first base. The base of the first jaw may define the first engagement surface. The first and second jaws can be configured to move in the lateral direction and in a transverse direction that is substantially perpendicular to the transverse direction.

The first jaw assembly may include a first handle member that is coupled to the first jaw. The second jaw assembly may include a second handle member that is coupled to the second jaw. In operation, the movement of the first and second handle members toward each other causes the first and second jaws to move toward each other. The bending tool may further include a biasing member that is connected between the first handle member and the second handle member to bias the first and second handle members away from each other. The second jaw assembly further comprising a jaw fastener that is connected between the adjustment member and the base. The jaw fastener can be configured to move between an unlocked position and a locked position to fix a position of the adjustment member relative to the base. In operation, moving the first and second jaw assemblies relative to each other cause at least one of the first and second jaws to move in a second lateral direction opposite the first lateral direction so as to increase the adjustment distance.

In an embodiment, the bending tool includes a first jaw assembly and a second jaw assembly. The first jaw assembly includes a first jaw. The second jaw assembly includes a second jaw. The second jaw assembly is movably coupled to the first jaw assembly such that the first jaw is movable with respect to the second jaw so as to at least partially define a gap. The gap is disposed between the first jaw and the second jaw. In operation, moving the first and second jaw assemblies relative to each other causes at least one of the first and second jaws to move in lateral and transverse directions toward each other, thereby causing the first and second jaws to apply a force to a portion of the orthopedic implant that is disposed in the gap to bend the orthopedic implant such that the first implant portion is offset relative to the second implant portion by an offset distance. The lateral direction may be substantially perpendicular to the transverse direction.

The present disclosure also relates to methods for bending an orthopedic implant with a bending tool including a first jaw assembly and a second jaw assembly. The first jaw assembly includes a first base and a first adjustment member that is movably coupled to the first base. The first base defines a first engagement surface. The second jaw assembly is moveably coupled to the first jaw assembly and includes a second base and a second adjustment member that is movably coupled to the second base. The second adjustment member defines a second engagement surface. An adjustment distance is defined from the second engagement surface to the first engagement surface along a lateral direction. The method may include at least one of the following steps; (a) moving the second adjustment member relative to the second base from an initial position to an adjusted position to set the adjustment distance such that the bending tool is configured to bend the orthopedic implant at an offset distance that is defined by the adjustment distance; (b) positioning a portion of the orthopedic implant between the first jaw assembly and the second jaw assembly; and (c) moving the first jaw assembly and the second jaw assembly relative to each other so as to deform the portion of the orthopedic implant from a first shape to a second shape that is different from the first shape.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the invention, the drawings show an embodiment that is presently preferred. The invention is not limited, however, to the specific instrumentalities disclosed in the drawings. In the drawings:

FIG. 2A is a perspective view of the bending tool shown in FIG. 1A, the bending tool including the first and second jaw assemblies, the first jaw assembly including a first base and a first adjustment member movably coupled to the first base, and the second jaw assembly including a second base and a second adjustment member movably coupled to the second base;

FIG. 2B is a top view of the bending tool shown in FIG. 2A;

FIG. 3A is a front view of the bending tool shown in FIG. 2A, showing the first and second jaw assemblies in the open position, and the first adjustment member located in a first initial position;

FIG. 3B is a front view of the bending tool shown in FIG. 2A, showing the first and second jaw assemblies in the open position, and the first adjustment member in a first adjusted position;

FIG. 3C is a front view of the bending tool shown in FIG. 2A, showing the first and second jaw assemblies in the closed position, and the second adjustment member in a second initial position;

FIG. 3D is a front view of the bending tool shown in FIG. 2A, showing the first and second jaw assemblies in the closed position, and the second adjustment member in a second adjusted position;

FIG. 4A is a front view of the first and second jaw of a bending tool in accordance with an alternative embodiment of the present disclosure;

FIG. 4B is a perspective view of an engagement surface of the second jaw illustrated in FIG. 4A;

FIG. 5D is a top view of the bending mechanism of the bending tool shown in FIG. 5A;

FIG. 5E is a bottom view of the bending mechanism of the bending tool shown in FIG. 5A;

FIG. 5G is a perspective view of the bending mechanism of the bending tool shown in FIG. 5A, illustrating the orthopedic implant after being bent by the rollers;

FIG. 5H is a top view of the bending mechanism shown in FIG. 5G, depicting the rollers in the first position;

FIG. 5I is a top view of the bending mechanism shown in FIG. 5G, illustrating the rollers in the second position and the bent orthopedic implant.

DETAILED DESCRIPTION OF THE DRAWINGS

Figure 1A:
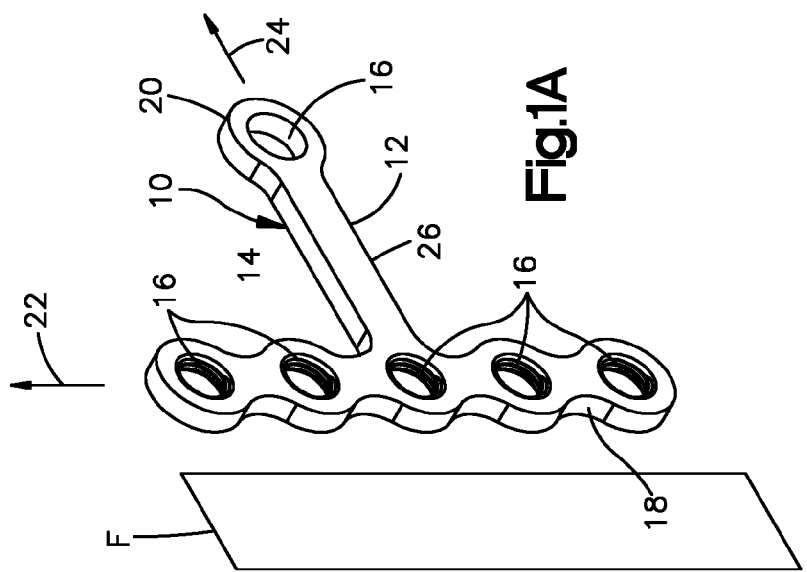
FIG. 1A is a perspective view of an orthopedic implant defining a first shape.
Figure 1B:
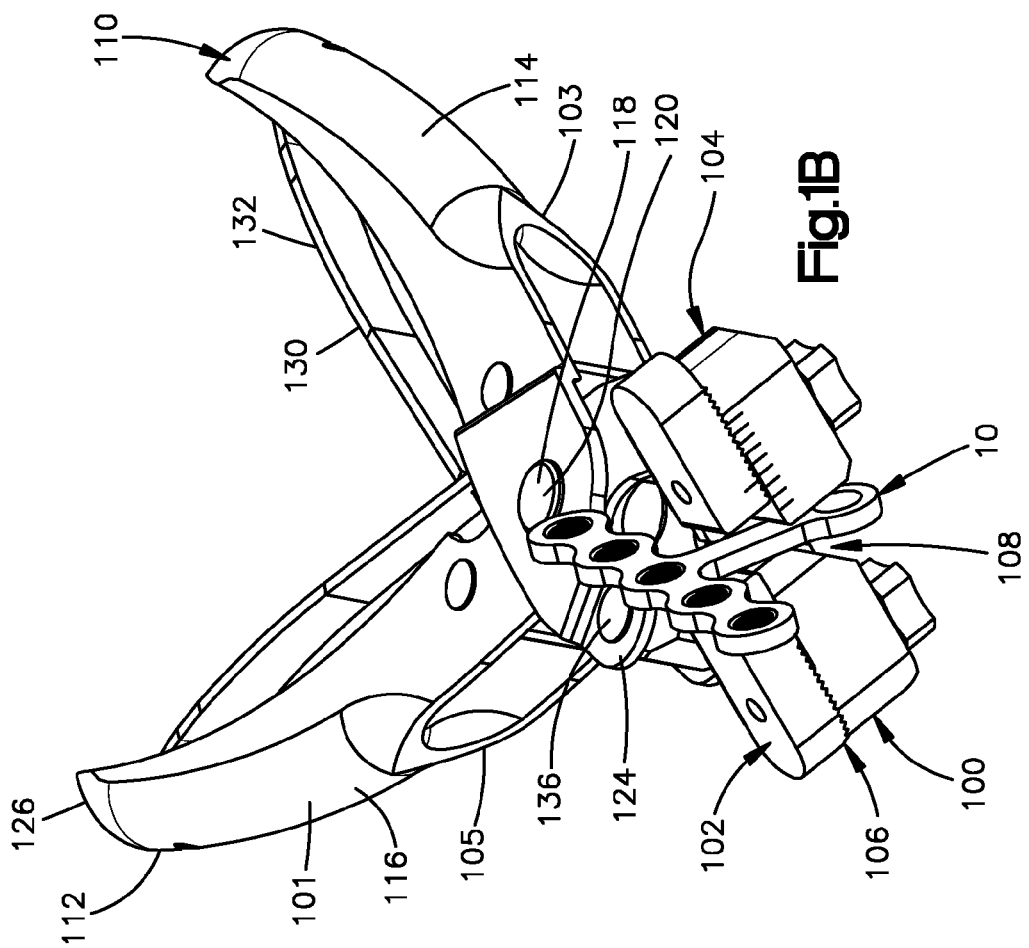
FIG. 1B is a perspective view of a bending tool that includes a first jaw assembly and a second jaw assembly, the first jaw assembly and the second jaw assembly in an open position, and the orthopedic implant shown in FIG. 1A is disposed in an implant receiving gap between the first and jaw assemblies.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device.

With reference to FIGS. 1A-D, the present disclosure relates to bending tools and methods for bending an orthopedic implant 10 at a predetermined offset. As used herein, the term "orthopedic implant" includes, but is not limited to, bone plates, wires, bending templates, or any other suitable apparatus or device that can be bent. The orthopedic implant 10 can be configured as a bone plate 12, such as orthognathic plate. For example, the orthopedic implant 10 may include an implant body 14 and one or more implant holes 16 that extend through the implant body 14. The implant holes 16 can be configured and sized to receive bone screws or any other suitable fastener. The bone screws can be inserted through the implant holes 16 and into a bone to fix the orthopedic implant 10 to said bone. The implant body 14 may include a first implant portion 18, a second implant portion 20, and a third implant portion 26 that is disposed between the first implant portion 18 and the second implant portion 20. The first implant portion 18 may be spaced from the second implant portion 20. In some embodiments, the second implant portion 20 and the third implant portion 26 may be elongate along a first implant direction 24, and the first implant portion 18 may be elongate along a second implant direction 22. The first implant direction 24 may be substantially perpendicular to the second implant direction 22. Alternatively, the first implant direction 24 may be angularly offset from the second implant direction 22 at an oblique angle. The orthopedic implant 10 may define a first shape as seen in FIG. 1A. For example, when the orthopedic implant 10 has the first shape, the implant body 14 may define a substantially planar configuration such that the implant body 14 substantially extends along a first implant plane F. Thus, when the orthopedic implant 10 has the first shape, the first implant portion 18, the second implant portion 20, and the third implant portion 26 may extend along the first implant plane F. As defined herein, the term substantially planar configuration includes, but is not limited to, a substantially flat configuration. Hence, the first shape of the orthopedic implant 10 may refer to a substantially planar configuration. However, the first shape of the orthopedic implant 10 may refer to other suitable shapes. A surgical kit may include a bending tool 100 (as described below) and the orthopedic implant 10. The surgical kit may be used to perform any suitable surgery such as orthognathic surgery.

In accordance with an embodiment of the present disclosure, the bending tool 100 can be configured as bending pliers 101. Irrespective of its specific configuration, the bending tool 100 is configured to bend the orthopedic implant 10 or any other suitable implant at a predetermined offset. The bending tool 100 may be partly or wholly made of a substantially rigid material such as a metal. In the depicted embodiment, the bending tool 100 includes a first jaw assembly 103 and a second jaw assembly 105 that is movably coupled to the first jaw assembly 103. In the depicted embodiment, the first jaw assembly 103 can be pivotally coupled to the second jaw assembly 105. The first jaw assembly 103 and the second jaw assembly 105 collectively form a bending mechanism 102 that is configured to bend the orthopedic implant 10. The bending mechanism 102 may include a first jaw 106 and a second jaw 104. The movement of the first jaw assembly 103 and the second jaw assembly 105 causes the first jaw 106 and the second jaw 104 to move toward or away from each other. In particular, the first jaw 106 and the second jaw 104 are configured to move toward and away from each other between an open position and a closed position. For instance, the first jaw 106 and the second jaw 104 can move toward and away from each other along an arched-shaped path. In the open position, the first jaw 106 and the second jaw 104 can collectively define an implant receiving gap 108. The implant receiving gap 108 is defined between the first jaw 106 and the second jaw 104 when the first jaw 106 and the second jaw 104 are in the open position. In the closed position, the first jaw 106 and the second jaw 104 are closer to each other than in the open position. In the depicted embodiment, the pivotal connection between the first jaw assembly 103 and the second jaw assembly 105 allows the first jaw 106 and the second jaw 104 to move toward and away from each other. Although the illustrated embodiments show a pivotal connection, it is envisioned that that the first jaw assembly 103 can be movably coupled to the second jaw assembly 105 by any suitable connection that allows the first jaw 106 and the second jaw 104 to move toward and away from each other. For example, the bending tool 100 may include a connection that allows the first jaw assembly 103 and the second jaw assembly 105 to move parallel to one another.

Figure 1D:
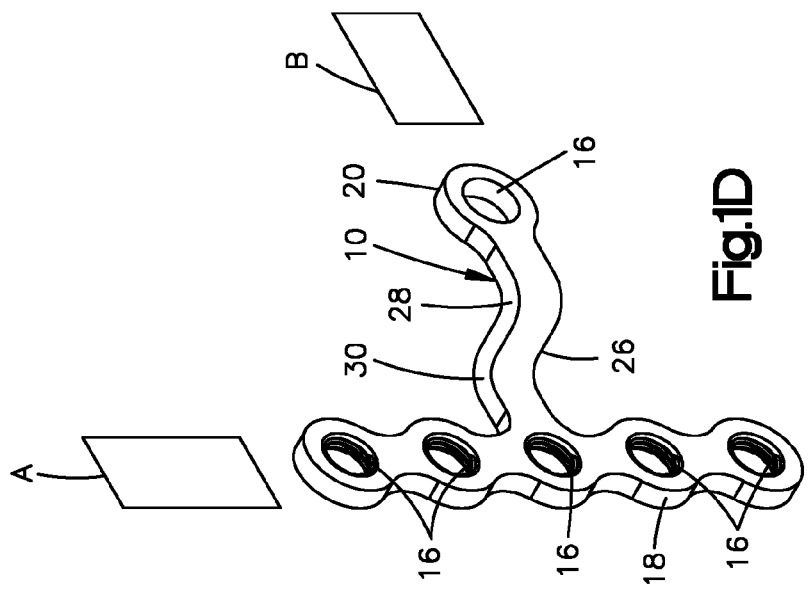
FIG. 1D is a perspective view of the bone shown in FIG. 1A defining a second shape.

In operation, at least a portion of the orthopedic implant 10 (or any other suitable implant) can be disposed in the implant receiving gap 108 while the first jaw 106 and the second jaw 104 are in the open position. Then, the first jaw 106 and the second jaw 104 can be moved toward the closed position (while at least a portion of the orthopedic implant 10 is in the implant receiving gap 108) to bend the orthopedic implant 10 at a desired offset. As the first jaw 106 and the second jaw 104 move from the open position toward the closed position, the bending mechanism 102 applies a force to the orthopedic implant 10 that is disposed in the implant receiving gap 108, causing the orthopedic implant 10 to deform from the first shape (FIG. 1A) to the second shape (FIG. 1D). The second shape (FIG. 1D) of the orthopedic implant 10 is different from the first shape (FIG. 1A). For example, when the orthopedic implant 10 has the second shape, the third implant portion 26 may define a first arch 28 and a second arch 30 such that the first implant portion 18 substantially extends along a first implant plane A and the second implant portion 20 substantially extends along a second implant plane B. The first implant plane A may be angularly offset relative to the second implant B. For example, the first implant plane A may be angularly offset relative to the second implant B at a right angle. Alternatively, the first implant plane A may be angularly offset relative to the second implant B at an oblique angle. As used herein, the term "oblique angle" refers to an angle, such as an acute or an obtuse angle, that is not a right angle or a multiple of a right angle. Consequently, the first implant portion 18 may be angularly offset relative to the second implant portion 20 when the orthopedic implant 10 has the second shape. Alternatively, the second shape of the orthopedic implant 10 may include other shapes that are different from the first shape. For example, the first shape, the second shape, or both may be anatomic in form. That is, at least a portion of the orthopedic implant 10 may be contoured to fit over a portion of an anatomy. For instance, at least a portion of the orthopedic implant 10 may be curved to fit over a particular portion of an anatomy. The angular offset of the first implant portion 18 relative to the second implant portion 20 can be determined before using the bending tool 100 to bend the orthopedic implant 10 by adjusting the first jaw 106, the second jaw 104, or both.

With reference to FIGS. 2A-D, the bending tool 100 includes an actuation mechanism 110 operatively coupled to the bending mechanism 102 such that actuation of the actuation mechanism 110 causes the first jaw 106 and the second jaw 104 to move between the open position and the closed position. The first jaw assembly 103 and the second jaw assembly 105 can cooperate to define the actuation mechanism 110. Similarly, the first jaw assembly 103 and the second jaw assembly 105 can cooperate to define the bending mechanism 102. The actuation mechanism 110 may be configured as a handle 112 that is connected to the first jaw 106 and the second jaw 104. In operation, the actuation of the handle 112 causes the first jaw 106 and the second jaw 104 to move between the open position and the closed position. In the depicted embodiment, the handle 112 may include a first handle member 114 and a second handle member 116. The first handle member 114 may be coupled to the first jaw 106, and the second handle member 116 may be coupled to the first jaw 106. The first jaw assembly 103 may include the first handle member 114 and the first jaw 106, while the second jaw assembly 105 may include the second handle member 116 and the second jaw 104.

The first handle member 114 defines a first or proximal handle end 122 and a second or distal handle end 124 that is spaced from the first handle end 122. Similarly, the second handle member 116 may define a first or proximal end 126 and a second handle end 128 that is spaced from the first handle end 126. A pivot member 118, such as a pivot pin, may pivotally connect the first handle member 114 to the second handle member 116. Generally, the pivot member 118 may pivotally couple the first jaw assembly 103 with the second jaw assembly 105. Thus, the first handle member 114 can be pivotally connected to the second handle member 116. Consequently, the first handle member 114 and the second handle member 116 can be configured to pivot relative to each other about a pivot axis P defined by the pivot member 118. The pivot member 118 can be configured as a pivot pin 120 that pivotally interconnects the first handle member 114 and the second handle member 116. In the depicted embodiment, the pivot member 118 can pivotally couple the first handle member 114 to the second handle member 116 at a location between the first handle end 122 and second handle end 124 and between the first handle end 126 and the second handle end 128. As a result, movement of the first handle ends 122, 126 of the first and second handle members 114, 116, respectively, toward each other causes the second handle ends 124, 128 of the first and second handle members 114, 116, respectively, to move toward each other. Conversely, movement of the first handle ends 122, 126 of the first and second handle members 114, 116, respectively, away from other causes the second handle ends 124, 128 of the first and second handle members 114, 116, respectively, to move away each other. Thus, the first handle member 114 and the second handle member 116 can move between a first handle position and a second handle position. In the second handle position, the first handle end 122 and the first handle end 126 are closer together than in the first handle position. Further, when the first handle member 114 and the second handle member 116 are in the second handle position, the second handle end 124 and the second handle end 128 are closer to each other than in the first handle position. The first handle position can also be referred to as the non-actuated position, and the second handle position can also be referred to as the actuated position. Hence, the first handle member 114 and the second handle member 116 can move between the non-actuated position and the actuated position.

The second handle end 124 of the first handle member 114 can be coupled to the first jaw 106, and the second handle end 128 of the second handle member 116 can be coupled to the second jaw 104. Consequently, movement of the first handle member 114 and the second handle member 116 between the first handle position and the second handle position causes the first jaw 106 and the second jaw 104 to move between the open position and the closed position. In the depicted embodiment, movement of the first handle member 114 and the second handle member 116 from the first handle position to the second handle position causes the first jaw 106 and the second jaw 104 to move from the open position to the closed position. Conversely, movement of the first handle member 114 and the second handle member 116 from the second handle position to the first handle position causes the first jaw 106 and the second jaw 104 to move from the closed position to the first position. In operation, forces H can be applied to the first handle member 114 and the second handle member 116 in the direction indicated by arrows H to move first handle end 122 and the first handle end 126 toward each other, causing the second handle end 124 and the second handle end 128 to move toward each other. Therefore, the application of forces H to the first handle member 114 and the second handle member 116 causes the first jaw 106 and the second jaw 104 to move from the open position to the closed position.

The handle 112 may further include a biasing member 130 that is connected between the first handle member 114 and the second handle member 116. The biasing member 130 may be configured as a spring 132 and can exert a biasing force on the first handle member 114 and the second handle member 116 in order to bias the first handle member 114 and the second handle member 116 toward the first handle position. In other words, the biasing member 130 can bias the first handle end 122 and the first handle end 126 away from each other. Thus, to move the first handle member 114 and the second handle member 116 from the first handle position toward the second handle position, the forces H applied to the first handle member 114 and the second handle member 116 should overcome the biasing force exerted by the biasing member 130 on the first handle member 114 and the second handle member 116. In the depicted embodiment, the biasing member 130 includes first biasing portion 131 that is attached to the first handle member 114 and a second biasing portion 133 that is attached to the second handle member 116. The first biasing portion 131 and the second biasing portion 133 are coupled to each other at a location between the first handle member 114 and the second handle member 116.

The bending tool 100 may further include a first connection arm 134 that couples the first handle member 114 to the first jaw 106. One or more fasteners 136, such as pins, screws or the like, may couple the second handle end 124 of the first handle member 114 to the first connection arm 134. The first connection arm 134 may also be movably coupled to the second handle member 116 to enhance the structural stability of the bending tool 100. One or more fasteners 138, such as a pin, may movably couple the first connection arm 134 to the second handle member 116. The first connection arm 134 may define a first groove 135 that is configured and sized to slidably receive the fastener 138. The pivotal movement of the first jaw assembly 103 and the second jaw assembly 105 causes the first connection arm 134 to move relative to the fastener 138 since the fastener 138 is slidably received in the first groove 135.

In addition to the first connection arm 134, the bending tool 100 may include a second connection arm 140 that couples the second handle member 116 to the second jaw 104. One or more fasteners 142, such as pins, screws, or the like, may couple the second handle end 128 of the second handle member 116 to the second connection arm 140. The second connection arm 140 may also be movably coupled to the first handle member 114 to enhance the structural stability of the bending tool 100. One or more fasteners 144 may movably couple the second connection arm 140 to the first handle member 114. The second connection arm 140 may define a second groove 145 that is configured and sized to slidably receive the fastener 144. The pivotal movement of the first jaw assembly 103 and the second jaw assembly 105 causes the second connection arm 140 to move relative to the fastener 144 since the fastener 144 is slidably received in the second groove 145. The connection between the second groove 145 and the fastener 144 and the connection between the first groove 135 and the fastener 138 allows the first jaw 106 and the second jaw 104 to move in transverse directions and lateral directions as described in detail below.

Figure 2C:
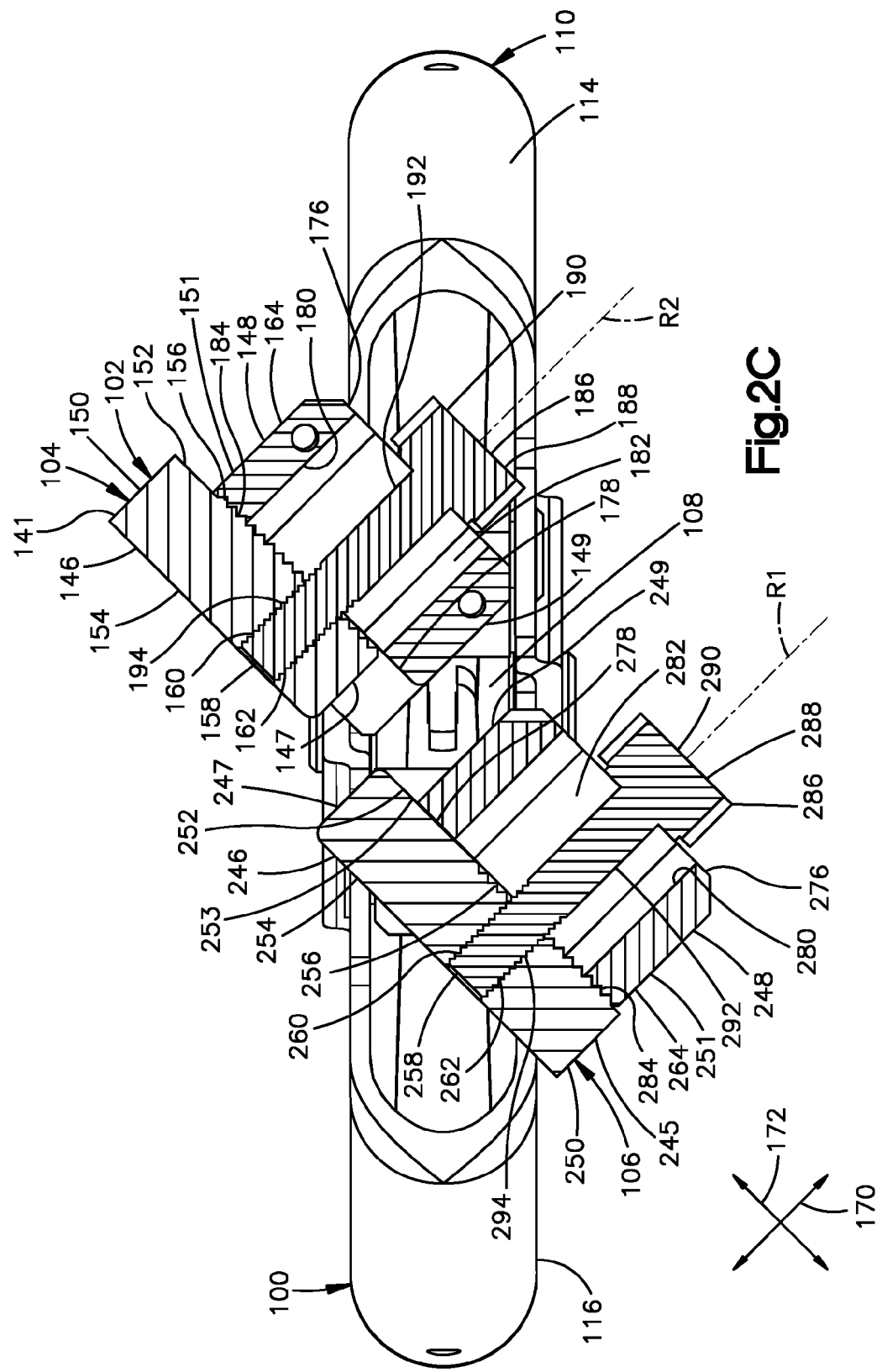
FIG. 2C is a front cross-sectional view of the bending tool shown in FIG. 2A, taken along section line 2C-2C of FIG. 2B.
Figure 2D:
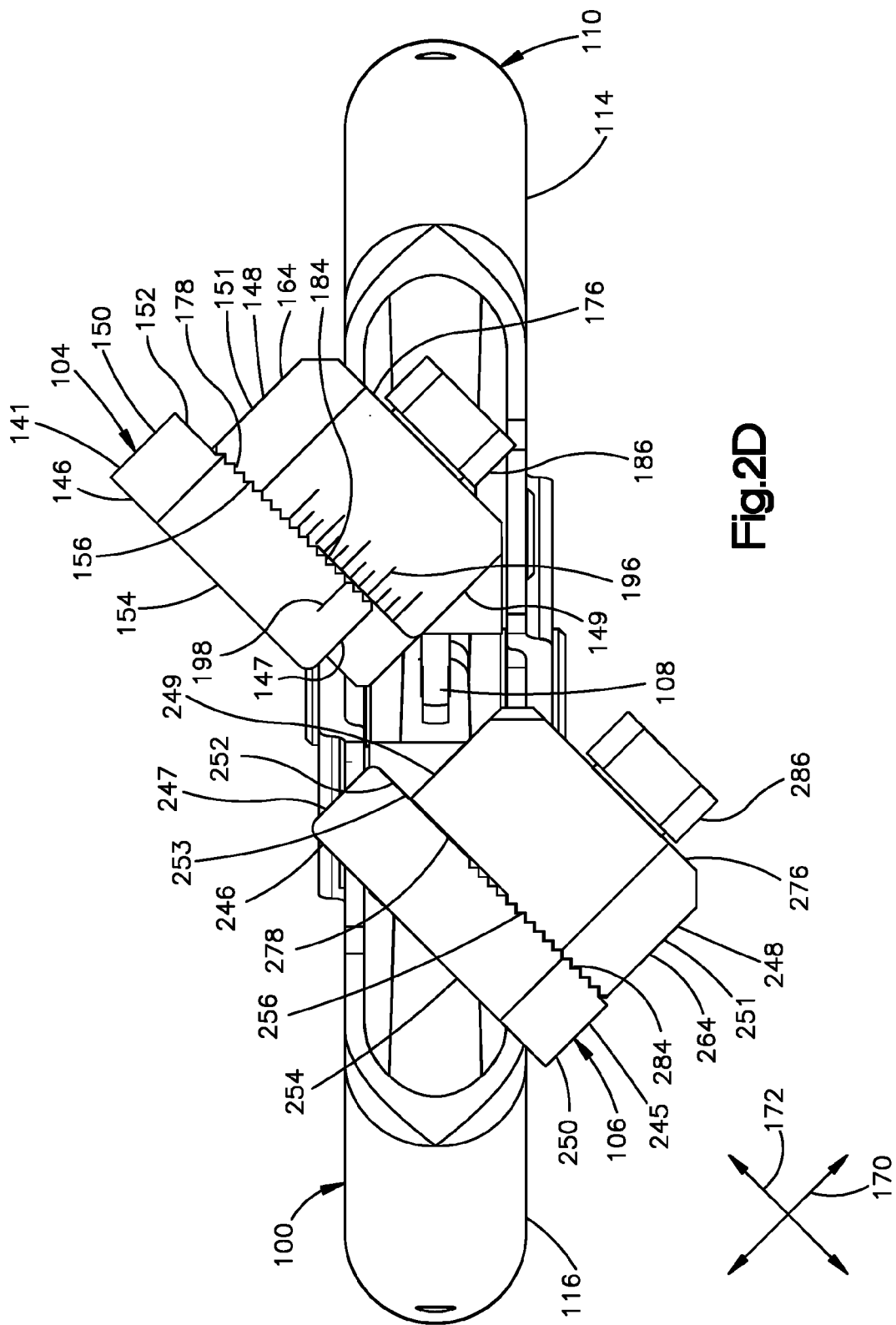
FIG. 2D is a front view of the bending tool shown in FIG. 2A.

With reference to FIG. 2C, the first jaw 106 is coupled to the first handle member 114 and may include a first adjustment member 246 and a first base 248 movably coupled to the first adjustment member 246. The first adjustment member 246 includes a first adjustment body 250 that may be elongate along a lateral direction 172, such as a first lateral direction or a second lateral direction opposite the first lateral direction. The first adjustment body 250 defines a first adjustment bottom surface 252 and an opposed first adjustment top surface 254. The first adjustment top surface 254 is spaced from the first adjustment bottom surface 252 along a transverse direction 170, such as first transverse direction or a second transverse direction opposite the first transverse direction. The transverse direction 170 may be substantially perpendicular to the lateral direction 172. At least a portion of the first adjustment bottom surface 252 can be configured to abut at least a portion of the first base 248. The first adjustment member 246 may further include one or more first adjustment teeth 256 that protrude from the first adjustment body 250. The first adjustment teeth 256 can be disposed along at least a portion of the first adjustment bottom surface 252. Specifically, the first adjustment teeth 256 may be spaced from one another along the lateral direction 172. The first adjustment member 246 may define a first adjustment hole 258 that extends between the first adjustment bottom surface 252 and the first adjustment top surface 254 along the transverse direction 170. The first adjustment hole 258 can be configured as a threaded hole. Further, the first adjustment member 246 may include a first adjustment inner surface 260 that defines the first adjustment hole 258. The first adjustment inner surface 260 may include first adjustment inner threads 262.

The first base 248 can be movably coupled to the first adjustment member 246 and fixed to the first connection arm 134. In the depicted embodiment, the first base 248 includes a first base body 264 that may be elongated along the lateral direction 172. The first base body 264 may define a first base bottom surface 276 and an opposed first base top surface 278. The first base bottom surface 276 may be spaced from the first base top surface 278 along the transverse direction 170. The first base 248 may further define a first base inner surface 280 that extends between the first base bottom surface 276 and the first base top surface 278. The first base inner surface 280 may define a first base slot 282 that extends into the first base body 264 between the first base bottom surface 276 and the first base top surface 278 along the transverse direction 170. The first base slot 282 may extend through the first base body 264 from the first base bottom surface 276 to the first base top surface 278 along the transverse direction 170. The first base slot 282 may be elongated along the lateral direction 172. Aside from the first base slot 282, the second base 148 may further include one or more first base teeth 284 that protrude from the first base body 264. The first base teeth 284 may be spaced from one another along the lateral direction 172. Moreover, the first base teeth 284 are configured to mate with the first adjustment teeth 256 such that the first adjustment member 246 can move incrementally relative to the first base 248. For example, the first adjustment member 246 can move relative to the first base 248 in about in one (1) millimeter increments.

The first jaw 106 further includes a first jaw fastener 286 that couples the first adjustment member 246 to the first base 248. The first jaw fastener 286 can be configured as a locking screw 288 or any other suitable fastener. In the depicted embodiment, the first jaw fastener 286 includes a first fastener head 290 and a first fastener shaft 292 that is connected to the first fastener head 290. The first fastener head 290 can be configured as a hex head. Further, the first fastener head 290 cannot fit inside the first base slot 282. In contrast, the first fastener shaft 292 can be configured and sized to fit inside the first base slot 282. The first fastener head 290 may further include first fastener external threads 294 disposed on the first fastener shaft 292. The first fastener external threads 294 can be configured to mate with the first adjustment inner threads 262 such that the first fastener shaft 292 can be coupled to the first adjustment member 246.

In operation, rotation of the first jaw fastener 286 about the first rotation axis R1 causes the first jaw fastener 286 to move between a first unlocked position and a first locked position. In the first unlocked position, the first jaw fastener 286 is coupled to the first adjustment member 246 but the first fastener shaft 292 can move along the first base slot 282 in the lateral direction 172. Accordingly, when the first jaw fastener 286 is in the first unlocked position, the first adjustment member 246 can be moved relative to the first base 248 via the first fastener head 290. For example, a user may manually move the first fastener head 290 to adjust the position of the first adjustment member 246 relative to the first base 248 when the first jaw fastener 286 is in the first unlocked position. Conversely, when the first jaw fastener 286 is in the first locked position, the first adjustment member 246 cannot move relative to the first base 248. In other words, the position of the first adjustment member 246 is fixed relative to the first base 248 when the first jaw fastener 286 is in the first locked position.

To move the first jaw fastener 286 from the first unlocked position to the first locked position, the first jaw fastener 286 can be rotated about the first rotation axis R1 in a first rotational direction. In particular, the rotation of the first jaw fastener 286 about the first rotation axis R1 in first rotational direction causes the first jaw fastener 286 to move in the transverse direction 170, thereby tightening first jaw fastener 286 between the first adjustment member 246 and the first base 248. When the first jaw fastener 286 is in the first locked position, the first fastener head 290 exerts pressure on the first base bottom surface 276, thereby precluding, or at least inhibiting, the first adjustment member 246 from moving relative to the first base 248.

To move the first jaw fastener 286 from the first locked position to the first unlocked position, the first jaw fastener 286 can be rotated about the rotation axis R1 in a second rotational direction that is opposite the first rotational direction. In particular, the rotation of the first jaw fastener 286 about the first rotation axis R1 in the second rotational direction causes the first jaw fastener 286 to move in the transverse direction 170, thereby loosening the first jaw fastener 286 from the first adjustment member 246. At this juncture, the first fastener shaft 292 can be move within the first base slot 282 in the lateral direction 172. The movement of the first fastener shaft 292 along the first base slot 282 in the lateral direction 172 causes the first adjustment member 246 to move relative to the first base 248 in the corresponding lateral direction 172 between a first initial position and a first adjusted position.

The first adjustment member 246 can move relative to the first base 248 between the first initial position and the first adjusted position to set the offset for the orthopedic implant 10 to be bent. To this end, the first base 248 may include a plurality of first base markings 296 that are spaced from one another along the first lateral direction or the second lateral direction 274. The first base markings 296 may correspond to a predetermined offset for the orthopedic implant 10. The first adjustment member 246 may also include at least one first adjustment marking 298 that can be aligned with any of the first base markings 296 to set the offset for the orthopedic implant 10 to be bent.

The first adjustment member 246 may define a first adjustment engagement surface and an opposed first outer surface 245 that is spaced from the first adjustment engagement surface 247 along the lateral direction 172. The first adjustment engagement surface 247 is configured to engage the orthopedic implant 10 when the orthopedic implant 10 is disposed in the implant receiving gap 108 and the first jaw 106 and the second jaw 104 move from the open position toward the closed position. The first adjustment engagement surface 247 can partially define the implant receiving gap 108. The first adjustment bottom surface 252 may include a first engagement portion 253 that is configured to engage the orthopedic implant 10 when the orthopedic implant 10 is disposed in the implant receiving gap 108 and the first jaw 106 and the second jaw 104 move from the open position toward the closed position. The first engagement portion 253 does not include teeth and can be configured as a substantially flat surface portion.

The first base 248 defines a first base engagement surface 249 and an opposed outer base surface 251 that is spaced from the first base engagement surface 249 along the lateral direction 172. The first base engagement surface 249 is configured to engage the orthopedic implant 10 when the orthopedic implant 10 is disposed in the implant receiving gap 108 and the first jaw 106 and the second jaw 104 move from the open toward the closed position. The first base engagement surface 249 can partially define the implant receiving gap 108.

With continuing reference to FIG. 2C, the structure and operation of the first jaw 106 and the second jaw 104 may be substantially similar or identical. In the depicted embodiment, the second jaw 104 is coupled to the second handle member 116 and may include a second adjustment member 146 and a second base 148 movably coupled to the second adjustment member 146. The second adjustment member 146 includes a second adjustment body 150 that may be elongate along the lateral direction 172. The second adjustment body 150 defines a second adjustment bottom surface 152 and an opposed second adjustment top surface 154. The second adjustment top surface 154 is spaced from the second adjustment bottom surface 152 along the transverse direction 170. At least a portion of the second adjustment bottom surface 152 can be configured to abut at least a portion of the second base 148. The second adjustment member 146 may further include one or more second adjustment teeth 156 that protrude from the second adjustment body 150. The second adjustment teeth 156 can be disposed along at least a portion of the second adjustment bottom surface 152. Specifically, the second adjustment teeth 156 may be spaced from one another along the lateral direction 172. The second adjustment member 146 may define a second adjustment hole 158 that extends between the second adjustment bottom surface 152 and the second adjustment top surface 154 along the transverse direction 170. The second adjustment hole 158 can be configured as a threaded hole. Further, the second adjustment member 146 may include a second adjustment inner surface 160 that defines the second adjustment hole 158. The second adjustment inner surface 160 may include second adjustment inner threads 162.

The second base 148 can be movably coupled to the second adjustment member 146 and fixed to the second connection arm 140. In the depicted embodiment, the second base 148 includes a second base body 164 that may be elongated along the lateral direction 172. The second base body 164 may define a second base bottom surface 176 and an opposed second base top surface 178. The second base bottom surface 176 may be spaced from the second base top surface 178 along the transverse direction 170. The second base 148 may further define a second base inner surface 180 that extends between the second base bottom surface 176 and the second base top surface 178. The second base inner surface 180 may define a second base slot 182 that extends into the second base body 164 between the second base bottom surface 176 and the second base top surface 178 along the transverse direction 170. The second base slot 182 may extend through the second base body 164 from the second base bottom surface 176 to the second base top surface 178 along the transverse direction 170. The second base slot 182 may be elongate along the lateral direction 172. In addition to the second base slot 182, the second base 148 may further include one or more second base teeth 184 that protrude from the second base body 164. The second base teeth 184 may be spaced from one another along the lateral direction 172. Moreover, the second base teeth 184 are configured to mate with the second adjustment teeth 156 such that the second adjustment member 146 can move incrementally relative to the second base 148. For example, the second adjustment member 146 can move relative to the second base 148 in about in one (1) millimeter increments.

The second jaw 104 further includes a second jaw fastener 186 that couples the second adjustment member 146 to the second base 148. The second jaw fastener 186 can be configured as a locking screw 188 or any other suitable fastener. In the depicted embodiment, the second jaw fastener 186 includes a second fastener head 190 and a second fastener shaft 192 that protrudes from the second fastener head 190. The second fastener head 190 can be configured as a hex head. Further, the second fastener head 190 cannot fit inside the second base slot 182. In contrast, the second fastener shaft 192 can be configured and sized to fit inside the second base slot 182. The second fastener head 190 may further include second fastener external threads 194 disposed on the second fastener shaft 192. The second fastener external thread 194 can be configured to mate with the second adjustment inner threads 162 such that the second fastener shaft 192 can be coupled to the second adjustment member 146.

In operation, rotation of the second jaw fastener 186 about the second rotation axis R2 causes the second jaw fastener 186 to move between a second unlocked position and a second locked position. In the second unlocked position, the second jaw fastener 186 is coupled to the second adjustment member 146 but the second fastener shaft 192 can move along the second base slot 182 in the first lateral direction or the second lateral direction. Accordingly, when the second jaw fastener 186 is in the second unlocked position, the second adjustment member 146 can be moved relative to the second base 148 via the second fastener head 190. For example, a user may manually move the second fastener head 190 to adjust the position of the second adjustment member 146 relative to the second base 148 when the second jaw fastener 186 is in the second unlocked position. Conversely, when the second jaw fastener 186 is in the second locked position, the second adjustment member 146 cannot move relative to the second base 148. In other words, the position of the second adjustment member 146 is fixed relative to the second base 148 when the second jaw fastener 186 is in the second locked position.

To move the second jaw fastener 186 from the second unlocked position to the second locked position, the second jaw fastener 186 can be rotated about the second rotation axis R2 in a first rotational direction. In particular, the rotation of the second jaw fastener 186 about the second rotation axis R2 in first rotational direction causes the second jaw fastener 186 to move in the transverse direction 170, thereby tightening second jaw fastener 186 between the second adjustment member 146 and the second base 148. When the second jaw fastener 186 is in the locked position, the second fastener head 190 exerts pressure on the second base bottom surface 176, thereby precluding, or at least inhibiting, the second adjustment member 146 from moving relative to the second base 148.

To move the second jaw fastener 186 from the locked position to the second unlocked position, the second jaw fastener 186 can be rotated about the second rotation axis R2 in a second rotational direction that is opposite the first rotational direction. In particular, the rotation of the second jaw fastener 186 about the second rotation axis R2 in the second rotational direction causes the second jaw fastener 186 to move in the transverse direction 170, thereby loosening the second jaw fastener 186 from the second adjustment member 146. At this juncture, the second fastener shaft 192 can be move within the second base slot 182 in the lateral direction 172. The movement of the second fastener shaft 192 along the second base slot 182 in the lateral direction 172 causes the second adjustment member 146 to move relative to the second base 148 in the corresponding lateral direction 172 between a second initial position and a second adjusted position.

The second adjustment member 146 may define a second adjustment engagement surface 147 and an opposed second outer surface 141 that is spaced from the second adjustment engagement surface 147 along the lateral direction 172. The second adjustment engagement surface 147 is configured to engage the orthopedic implant 10 when the orthopedic implant 10 is disposed in the implant receiving gap 108 and the first jaw 106 and the second jaw 104 move from the open position toward the closed position. The second adjustment engagement surface 147 can partially define the implant receiving gap 108. The second base 148 defines a second base engagement surface 149 and an opposed outer base surface 151 that is spaced from the second base engagement surface 149 along the lateral direction 172. The second base engagement surface 149 is configured to engage the orthopedic implant 10 when the orthopedic implant 10 is disposed in the implant receiving gap 108 and the first jaw 106 and the second jaw 104 move from the open toward the closed position. The second adjustment engagement surface 147 can partially define the implant receiving gap 108.

Figure 1C:
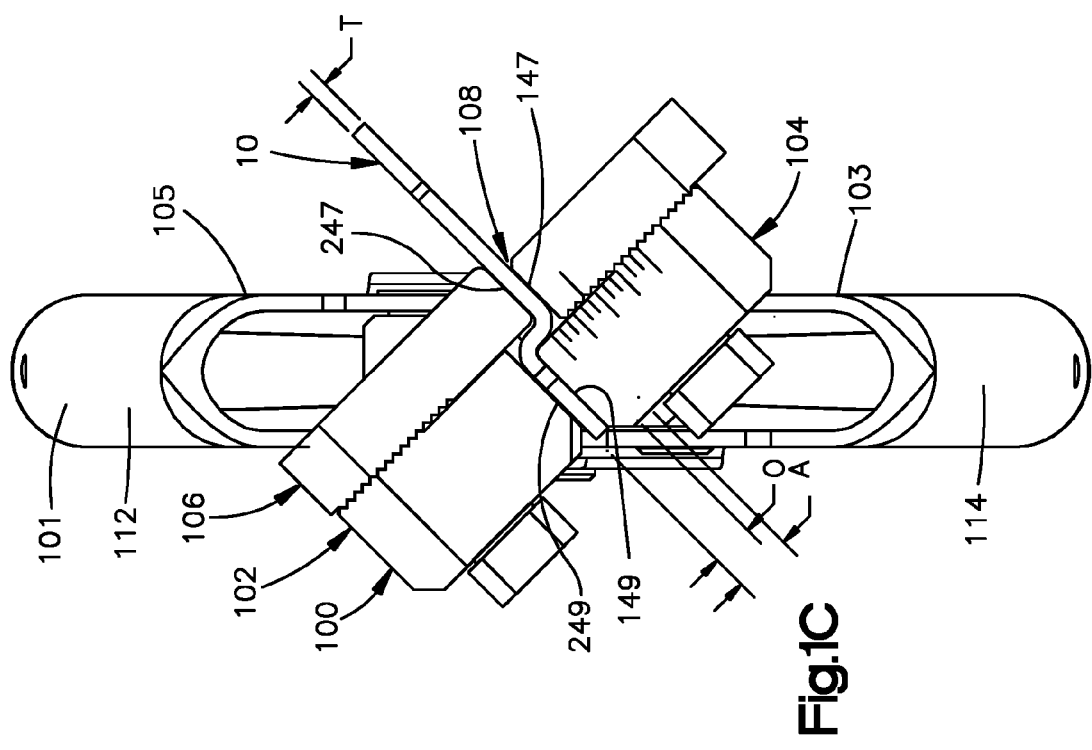
FIG. 1C is a front view of the bending tool shown in FIG. 1B, the bone plate disposed in the bone plate receiving gap, and the first and second jaw assemblies in a closed position so that the bone plate can acquire a second shape.

With reference to FIG. 1C, the bending tool 100 can bend the orthopedic implant 10 at a predetermined offset. This predetermined offset distance O is defined by an adjustment distance A that is defined from the second adjustment engagement surface 147 to the first base engagement surface 249 minus a thickness T of the orthopedic implant 10. It is envisioned that the thickness T may represent that thickness of the portion of the orthopedic implant 10 that is disposed in the implant receiving gap 108. Thus, the predetermined offset distance O can be defined as the adjustment distance A minus the thickness T. The adjustment distance A can be changed by moving the second adjustment member 146 relative to the second base 148. The adjustment distance A can also be changed by moving the first adjustment member 246 relative to the first base 248. That is, the adjustment distance A can be a variable adjustment distance. Thus, the bending tool 100 can bend the orthopedic implant 10 so that the first implant portion 18 can be offset from the second implant portion 20 by the predetermined offset distance O.

Figure 3E:
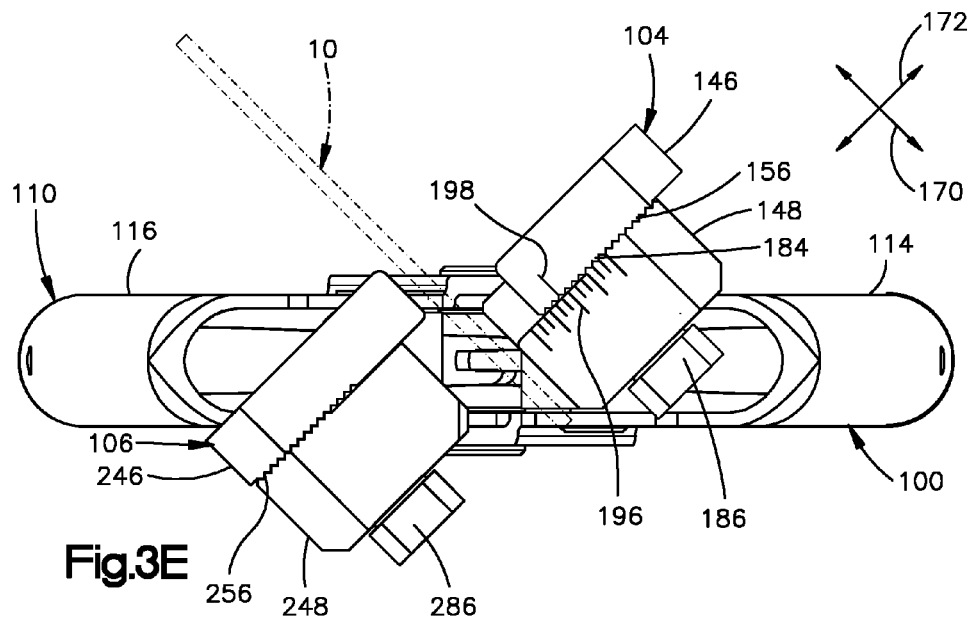
FIG. 3E is a front view of the bending tool shown in FIG. 2A, showing the first and second jaw assemblies in the open position, the first adjustment member in the first adjusted position, and the second adjustment member in the second adjusted position.
Figure 3F:
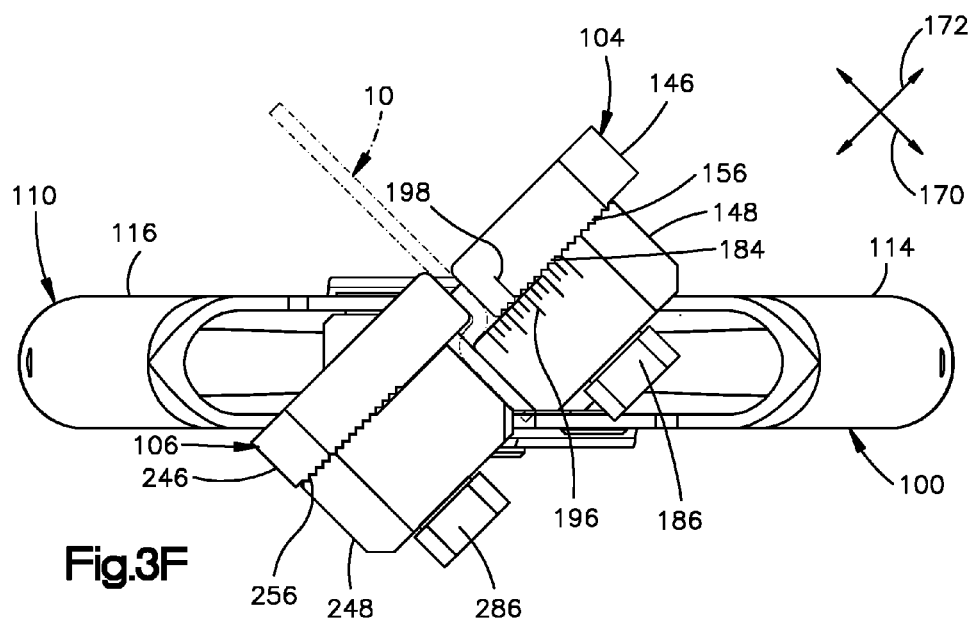
FIG. 3F is a front view of the bending tool shown in FIG. 2A, showing the first and second jaw assemblies in the closed position, the first adjustment member in the first adjusted position, and the second adjustment member in the second adjusted position.

With continuing reference to FIGS. 3A-D, the bending tool 100 can be used to bend the orthopedic implant 10 at a predetermined offset. To do so, a user may perform one or more of the following steps. Initially, the first jaw fastener 286 should be in the first unlocked position, and the second jaw fastener 186 should be in the second unlocked position. The first adjustment member 246 can be located in the second initial position and the first jaw 106 and the second jaw 104 can be in the open position as shown in FIG. 3A. The second adjustment member 146 can then be moved relative to the second base 148 from the second initial position (FIG. 3A) to the second adjusted position (FIG. 3B). For example, the user may first determine the desired offset for the orthopedic implant 10. Then, the marking 196 that corresponds to the desired offset for the orthopedic implant 10 is identified. To move the second adjustment member 146 from the second initial position to the second adjusted position, the second adjustment member 146 can be moved relative to the second base 148 along the lateral direction 172 until an adjustment marking 198 is substantially aligned with a base marking 196 identified for the desired offset for the orthopedic implant 10 while the first jaw 106 and the second jaw 104 are in the open position. Alternatively, the second adjustment member 146 can be moved relative to the second base 148 along the lateral direction 172 until the adjustment marking 198 is substantially aligned with the base marking 196 identified for the desired offset for the orthopedic implant 10 while the first jaw 106 and the second jaw 104 are in the open position. Once the second adjustment member 146 is located in the second adjusted position (FIG. 3B), the second jaw fastener 186 can be moved from the second unlocked position to the second locked position to fix the position of the second adjustment member 146 relative to the second base 148. As discussed above, the second jaw fastener 186 can be moved from the second unlocked position to the second locked position by rotating it about the first rotation axis R1.

The first jaw 106 and the second jaw 104 can then be moved from the open position to the closed position as shown in FIG. 3C. As the first jaw 106 and the second jaw 104 move toward closed position, the first jaw 106 and the second jaw 104 can move in the transverse direction 170 and in the lateral direction 172. The actuation mechanism 110 can be actuated to move the first jaw 106 and the second jaw 104 from the open position to the closed position. In particular, as discussed above, forces H can be applied to the first handle member 114 and the second handle member 116 to move the first jaw 106 and the second jaw 104 from the open position to the closed position. It is envisioned, however, that the handle 112 can be actuated in other manners to move the first jaw 106 and the second jaw 104 from the open position to the closed position. Thus, the handle 112 can be actuated to move the first jaw 106 and the second jaw 104 from the open position to the closed position. At this juncture, at least a portion of the second base 148 may abut at least a portion of the first base 248, but the second adjustment member 146 does not necessarily abuts the first adjustment member 246.

Next, the first adjustment member 246 can be moved from the first initial position (FIG. 3C) to the first adjusted position (FIG. 3D). In the first initial position, the first adjustment member 246 does not necessarily contact the second adjustment member 146. Conversely, in the first adjusted position, the first adjustment member 246 can contact the second adjustment member 146. Thus, to move the first adjustment member 246 from the first initial position to the first adjusted position, the first adjustment member 246 can be move relative to the first base 248 in the lateral direction 172 until at least a portion of the first adjustment member 246 contacts at least a portion of the second adjustment member 146. Then, the first jaw fastener 286 can be moved from the first unlocked position to the first locked position to fix the position of the second adjustment member 246 relative to the first base 248. As discussed above, the first jaw fastener 286 can be moved from the first unlocked position to the first locked position by rotating it about the second rotation axis R1. At this juncture, the bending tool 100 is prepared for bending the orthopedic implant at the predetermined offset.

The first jaw 106 and the second jaw 104 can be moved from the closed position to the open position. Then, at least a portion of the orthopedic implant 10 can be positioned in the implant receiving gap 108 between the first jaw 106 and the second jaw 104. Next, the handle 112 can be actuated to move the first jaw 106 and the second jaw 104 toward each other from the open position toward the closed position. As the first jaw 106 and the second jaw 104 move from the open position toward the closed position, the first jaw 106 and the second jaw 104 apply a force to the orthopedic implant 10, thereby deforming the orthopedic implant 10 from the first shape (FIG. 1A) to the second shape (FIG. 1D).

With reference to FIG. 4A, an alternative embodiment of a bending tool may include a first jaw 306 and a second jaw 304. The structure and operation of the bending tool illustrated in FIG. 4A is substantially similar to the bending tool 100 described above with respect to FIGS. 1A-3F. Thus, in the interest of brevity, only structure and operation of the first jaw 306 and the second jaw 304 are described in detail.

The first jaw 306 includes a first base 348 and a first adjustment member 346 that is movably coupled to the first base 348. The first base 348 includes a first base body 364 that may be elongate along the lateral direction 172 and a base support member 368 that protrudes from the first base body 364. The first base body 364 defines a first base engagement surface 349 and an opposed first base outer surface 351 that is spaced from the first base engagement surface 349 along the lateral direction 172. Further, the base body 364 defines a first base bottom surface 376 and a first base top surface 378 that is spaced from the first base bottom surface 376 along the transverse direction 170. The base support member 368 may protrude from the first base body 364 in the transverse direction 170. Specifically, the base support member 368 may protrude outwardly from the first base top surface 378. Further, the base support member 368 may be elongate along the transverse direction 170. The first base 348 further defines a first bore 370 that extends through the base support member 368. The first bore 370 may extend through the base support member 368 along the lateral direction 172. A first inner base surface 372 of the base support member 368 may define the first bore 370 and is configured and sized to receive a portion of the first adjustment member 346.

In the depicted embodiment, the first inner base surface 372 may be configured as a threaded inner surface. Accordingly, the first base 348 includes inner threads 374 disposed around the first bore 370. The first adjustment member 346 includes a first adjustment body 350 and a first elongated member 302 that is translatably fixed to the first adjustment body 350, such that as the first elongated member 302 travels along the lateral direction 172, the first elongated member 302 travels along the lateral direction 172 simultaneously with the first elongated member 302. Furthermore, the first elongated member 302 can be rotatable with respect to the first adjustment body 350 about an axis of rotation 333 that can extend along the lateral direction 172. The first elongated member 302 can be configured as a threaded screw having threads that mate with the threads 374 of the base support member 368, such that rotation of the first elongated member 302 relative to the base support member 368 in a first direction about the axis of rotation 333 causes the first adjustment body 350 to advance forward, or toward the second adjustment body 450 along the lateral direction 172, and rotation of the first elongated member 302 relative to the base support member 368 in a second direction about the axis of rotation 333 opposite the first direction causes the first adjustment body 350 to retract rearward, or away from the second adjustment body 450 along the lateral direction 172. The threads of the first elongated member 302 can have any pitch as desired. For instance, in one embodiment, each complete revolution of the first elongated member can move the first adjustment body 350 any distance as desired, such as 1 mm.

The first base 348 may include at least one protrusion 311 that protrudes from the first inner base surface 372 and into the first bore 370. In the depicted embodiment, the first base 348 may include one protrusion 311 that extends into the bore 370 along a direction that is substantially perpendicular to the lateral direction 172 and the transverse direction 170. The protrusion 311 may be configured as a detent such as a ball detent that can ride along an engagement surface 373, which can be a flat or a surface having a curvature different than a remainder of the outer surface of the first elongated member 302. Accordingly, as the first elongated member 302 rotates relative to the base support member 368, engagement between the protrusion 311 and the engagement surface provides tactile feedback to the user at a predetermined interval of rotation. For instance, if the first adjustment member includes one protrusion 311 and one engagement surface, the tactile feedback can be provided at each revolution. If the first adjustment member 346 includes a pair of equidistantly spaced protrusions and/or engagement surfaces 373, the tactile feedback can be provided at each half-revolution.

The first adjustment body 350 may define a first engagement surface 353 and a first outer surface 355 that is opposite the first engagement surface 353 and spaced from the first engagement surface 353 along the lateral direction 172. Specifically, the first adjustment body 350 and the first elongated member 302 can be configured to move along the lateral direction 172. In the depicted embodiment, the first elongated member 302 may be elongate along the lateral direction 172 and may be configured as a shaft 304 or any other elongate member suitable to move along the lateral direction 172. The first elongate member 302 defines an outer surface 313 and external threads 315 disposed on the outer surface 313. The external threads 315 can be configured to mate with the inner threads 374 of the first base 348, thereby allowing the first elongated member 302 to move relative to the first base 348. Alternatively or additionally, the external threads 315 can be configured to mate with the protrusion 311, thereby allowing the first elongated member 302 to move relative to the first base 348. In operation, rotating the first elongated member 302 in a first direction causes the first elongated member 302 to move relative to the first base 348 toward the second jaw 304 along the lateral direction. Conversely, rotating the first elongated member 302 in a second direction, which is opposite the first direction, causes the first elongated member 302 to move relative to the first base 348 away from the second jaw 304 along the lateral direction 172. However, the engagement between the external threads 315 of the first elongated member 302 and the first inner threads 374 and/or the protrusion 311 prevents, or at least inhibits, the first elongated member 302 from moving relative to the first base 348 until a rotary force is applied to the first elongated member 302. As discussed above, the first adjustment member 346 includes a first adjustment body 350 that is coupled to the first elongated member 302. In operation, the first elongated member 302 can be rotated to move the first adjustment body 350 toward or away from the second jaw 304 along the lateral direction 172.

The first adjustment member 346 may further include a handle 319 that facilitates rotation of the first elongated member 302. The handle 319 can be configured as a knob and is attached to an end of the first elongated member 302. The handle 319 defines a stop member, such as a shoulder 321 that can have a dimension greater than that of the first elongated member 302 along a direction perpendicular to the axis of rotation 333. For instance, the shoulder 321 can have a diameter greater than that of the first elongated member 302. Thus, a user may rotate the first elongated member 302 via the knob. Instead of the handle 319, the adjustment member 349 may be a socket that is configured and sized to receive a driving tool. The handle 319 and the first elongated member 302 may rotate about a rotation axis 333. In this case, the user can use insert the driving tool into the socket and then use the driving tool to rotate the first elongated member 302.

The first adjustment body 350 is configured to slide along the first base top surface 378 along the lateral direction 172. The first adjustment body 350 can advance forward until the shoulder 321 abuts the base support member 368, such as an inner abutment surface 371 of the base support member 368, at which point the first adjustment body 350 is fully extended. The first adjustment body 350 can retract rearward until the first adjustment body 350 abuts the base support member 368, and in particular until the first outer surface 355 abuts the forward edge of the base support member 368, at which point the first adjustment body 350 is fully retracted. When the first adjustment body 350 is fully retracted, the first engagement surface 353 can define a predetermined positional relationship with respect to the first base engagement surface 349. For instance, the first engagement surface 353 can be substantially flush with the first base engagement surface 349, or can extend from the first base engagement surface a predetermined distance, such that the first engagement surface 353 abuts the second engagement surface 453 when the first and second base engagement surfaces 349 and 449 abut each other.

The second jaw 304 includes a second base 448 and an second adjustment member 446 that is coupled to the second base 448. The second base 448 includes a second base body 464 that may be elongate along the lateral direction 172 and a base support member 468 that protrudes from the second base body 464. The second base body 464 defines a second base engagement surface 449 and an opposed second base outer surface 451 that is spaced from the second base engagement surface 449 along the lateral direction 172. Further, the second base body 464 defines a first base bottom surface 476 and a second base top surface 478 that is spaced from the second base bottom surface 476 along the transverse direction 170. The base support member 468 may protrude from the second base body 464 in the transverse direction 170. Specifically, the base support member 468 may protrude outwardly from the second base top surface 478. Further, the base support member 468 may be elongate along the transverse direction 170. The second base 448 further defines a second bore 470 that extends through the base support member 468. The second bore 470 may extend through the base support member 468 along the lateral direction 172. A second inner base surface 472 of the base support member 468 may define the second bore 470 and is configured and sized to receive a portion of the second adjustment member 446. In the depicted embodiment, the second inner base surface 472 may be configured as a threaded inner surface. Accordingly, the second base 448 includes inner threads 474 disposed around the second bore 470.

The second adjustment member 446 includes a second adjustment body 450 and a second elongated member 402 that is translatably fixed to the second adjustment body 450, such that as the second elongated member 402 travels along the lateral direction 172, the second elongated member 402 travels along the lateral direction 172 simultaneously with the second elongated member 402. Furthermore, the second elongated member 402 can be rotatable with respect to the second adjustment body 450 about the axis of rotation 333. The second elongated member 402 can be configured as a threaded screw having threads that mate with the threads 474 of the base support member 468, such that rotation of the second elongated member 402 relative to the base support member 468 in a first direction about the axis of rotation 333 causes the second adjustment body 450 to advance forward, or toward the first adjustment body 350 along the lateral direction 172, and rotation of the second elongated member 402 relative to the base support member 468 in a second direction about the axis of rotation 333 opposite the first direction causes the second adjustment body 450 to retract rearward, or away from the first adjustment body 350 along the lateral direction 172. The threads of the second elongated member 402 can have any pitch as desired, such as a pitch equal to the pitch of the threads of the first elongated member 302. Thus, in one embodiment, each complete revolution of the second elongated member 402 can move the second adjustment body 450 any distance as desired, such as 1 mm.

The second base 448 may include at least one protrusion 411 that protrudes from the second inner base surface 472 and into the second bore 470. In the depicted embodiment, the second base 448 may include one protrusion 411 that extends into the bore 470 along a direction that is substantially perpendicular to the lateral direction 172 and the transverse direction 170. The protrusion 411 may be configured as a detent such as a ball detent that can ride along an engagement surface 473, which can be a flat or a surface having a curvature different than a remainder of the outer surface of the second elongated member 402. Accordingly, as the second elongated member 402 rotates relative to the base support member 468, engagement between the protrusion 411 and the engagement surface 473 provides tactile feedback to the user at a predetermined interval of rotation. For instance, if the first adjustment member includes one protrusion 411 and one engagement surface 473, the tactile feedback can be provided at each revolution. If the first adjustment member 446 includes a pair of equidistantly spaced protrusions and/or engagement surfaces 473, the tactile feedback can be provided at each half-revolution.

The second adjustment body 450 may define a second engagement surface 453 and a second outer surface 455 that is opposite the second engagement surface 453 and spaced from the second engagement surface 453 along the lateral direction 172. Specifically, the second adjustment body 450 and the second elongated member 402 can be configured to move along the lateral direction 172. In the depicted embodiment, the second elongated member 402 may be elongate along the lateral direction 172 and may be configured as a shaft 404 or any other elongate member suitable to move along the lateral direction 172. The second elongate member 402 defines an outer surface 413 and external threads 415 disposed on the outer surface 413. The external threads 415 can be configured to mate with the inner threads 474 of the second base 448, thereby allowing the second elongated member 402 to move relative to the second base 448. Alternatively or additionally, the external threads 415 can be configured to mate with the protrusion 411, thereby allowing the second elongated member 402 to move relative to the second base 448. In operation, rotating the second elongated member 402 in a first direction causes the second elongated member 402 to move relative to the second base 448 toward the first jaw 306 along the lateral direction 172. Conversely, rotating the second elongated member 402 in a second direction, which is opposite the first direction, causes the second elongated member 402 to move relative to the second base 448 away from the first jaw 306 along the lateral direction 172. However, the engagement between the external threads 415 of the second elongated member 402 and the second inner threads 474 and/or the protrusion 411 prevents, or at inhibits, the second elongated member 402 from moving relative to the second base 448 until a rotary force is applied to the second elongated member 402. As discussed above, the second adjustment member 446 includes the second adjustment body 450 that is coupled to the second elongated member 402. In operation, the second elongated member 402 can be rotated to move the second adjustment body 50 toward or away from the first jaw 306 along the lateral direction 172.

The second adjustment member 446 may further include a handle 419 that facilitates rotation of the first elongated member 302. The handle 419 can be configured as a socket and is attached to an end of the second elongated member 402. The handle 419 defines a stop member, such as a shoulder 421 that can have a dimension greater than that of the second elongated member 402 along a direction perpendicular to the axis of rotation 333. For instance, the shoulder 421 can have a diameter greater than that of the second elongated member 402. Thus, a user may rotate the second elongated member 402 via the handle 419. Either handle 419 can be a socket, a knob, or any alternative structure suitable for facilitating rotation. The handle 419 and the second elongated member 402 may rotate about the rotation axis 333. In this case, the user can use insert the driving tool into the socket and then use the driving tool to rotate the second elongated member 402.

The second adjustment body 450 is configured to slide along the second base top surface 478 along the lateral direction 172. The second adjustment body 450 can advance forward until the shoulder 421 abuts the base support member 468, such as an inner abutment surface 471 of the base support member 468, at which point the second adjustment body 450 is fully extended. The second adjustment body 450 can retract rearward until the second adjustment body 450 abuts the base support member 468, and in particular until the second outer surface 455 abuts the forward edge of the base support member 468, at which point the second adjustment body 450 is fully retracted. When the second adjustment body 450 is fully retracted, the second engagement surface 453 can define a predetermined positional relationship with respect to the second base engagement surface 449. For instance, the second engagement surface 453 can be substantially flush with the second base engagement surface 449, or can extend from the second base engagement surface 449 a predetermined distance, such that the second engagement surface 453 abuts the second engagement surface 453 when the first and second base engagement surfaces 349 and 449 abut each other.

The second adjustment body 450 can include at least one marker 456, and the second base body 464 can define a scale 466 that includes markings spaced from each other along the lateral direction 172 a predetermined distance, such as 1 mm. The scale 466 can be spaced from the second base engagement surface 449 by the predetermined distance, and the marker 456 can be spaced from the second engagement surface 453 by the predetermined distance, such that the second engagement surface 453 and the second base engagement surface 449 can be flush when the marker 456 is aligned with the first marking of the scale 466, indicating a zero offset. As the second adjustment body 450 is retracted rearward, the marker 456 moves relative to the scale 466 so that the offset may be measured based on the marking of scale 466 that is aligned with the marker 456.

Referring also to FIG. 4B, it should be appreciated that the second engagement surface 453 can define any geometry as desired, and the first engagement surface 453 can define any geometry as desired that is the inverse of the second engagement surface 453. For instance, the second engagement surface 453 can be substantially planar as illustrated in FIG. 4A, or can be non-planar, and can define any non-planar anatomical or organic geometry as desired. For instance, the non-planar geometry can be curved as illustrated in FIG. 4B, such as concave or convex, or define any other non-planar geometry that is to be imparted, for instance stamped, onto the orthopedic implant 10, such as the plate 12, that is received between the first and second engagement surfaces 453. Accordingly, when the first and second engagement surfaces 353 and 453 are brought together, the geometry of the first and second engagement surfaces 353 and 453 is imparted onto respective first and second opposed surfaces of the plate 12 that face the first and second engagement surfaces 453, respectively. Accordingly, the geometry imparted onto the first surface is the inverse of the geometry imparted onto the second surface.

With reference to FIGS. 5A-J, a bending tool 500 is configured to bend the orthopedic implant 10 or any other suitable implant at a predetermined offset. In the depicted embodiment, the bending tool 500 includes a tool body 502 and a handle 508 that protrudes from the tool body 502. The handle 508 may protrude in a transverse direction 512 and may feature an ergonomic design to facilitate grapping the handle 508. In the depicted embodiment, the handle 508 is elongate along the transverse direction 512. However, it is envisioned that the handle 508 may be elongate along other directions. For instance, the handle 508 may be elongate along a direction that defines an oblique angle relative to the transverse direction 512.

The bending tool 500 further includes a tool support member 510 that supports at least a portion of the bending mechanism 501. The tool support member 510 protrudes from the tool body 502 and may be elongate along a longitudinal direction 515 that is substantially perpendicular to the transverse direction 512. However, it is contemplated that the tool support member 510 may be elongate along other directions. Regardless, the tool support member 510 can physically support a bending mechanism 501 as well as other parts of the bending tool 500.

Figure 5A:
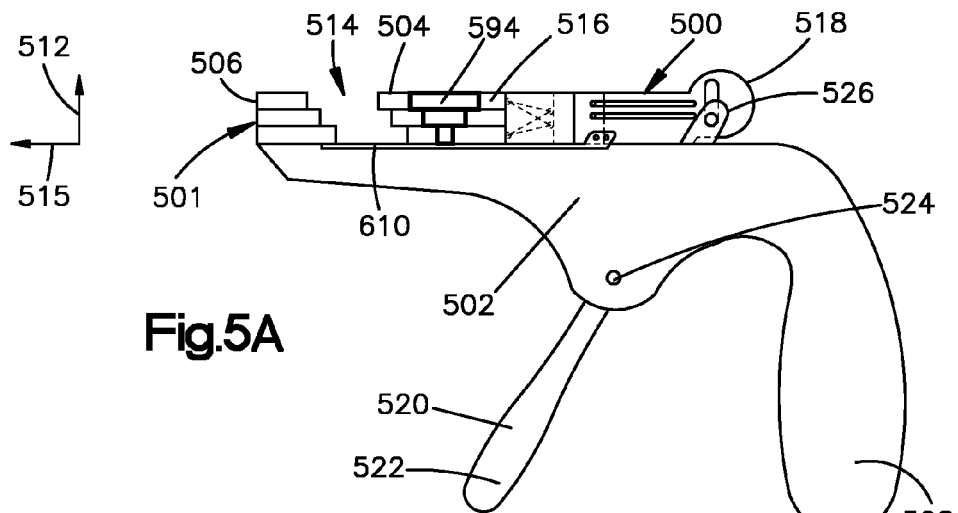
FIG. 5A is a side view of a bending tool in accordance with another embodiment of the present disclosure, the bending tool including a bending mechanism that has first and second jaws, and first and second rollers, wherein the first and second jaws are in a first or open position, and rollers are in a first position.
Figure 5B:
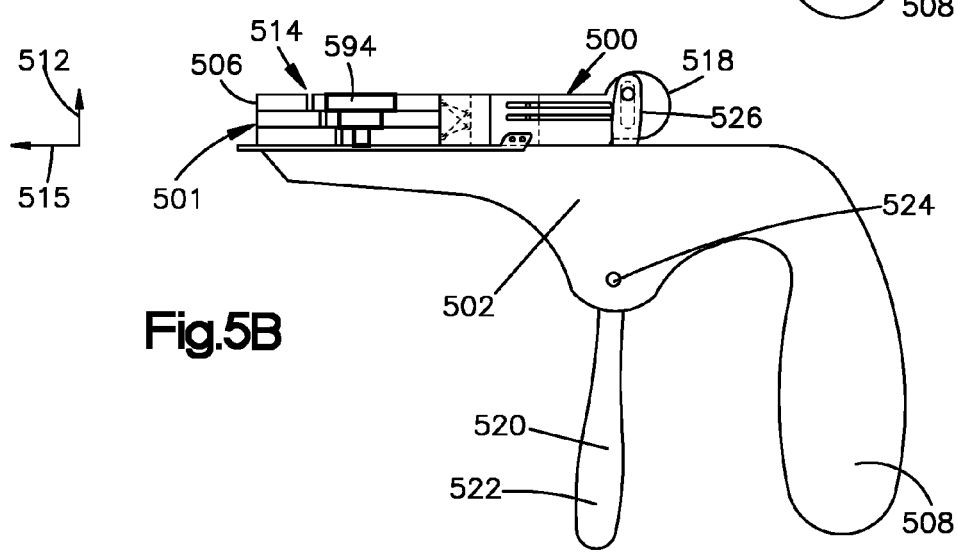
FIG. 5B is a side view of the bending tool of FIG. 5A, showing the first and second jaws in a second or closed position and the rollers in the first position.
Figure 5C:
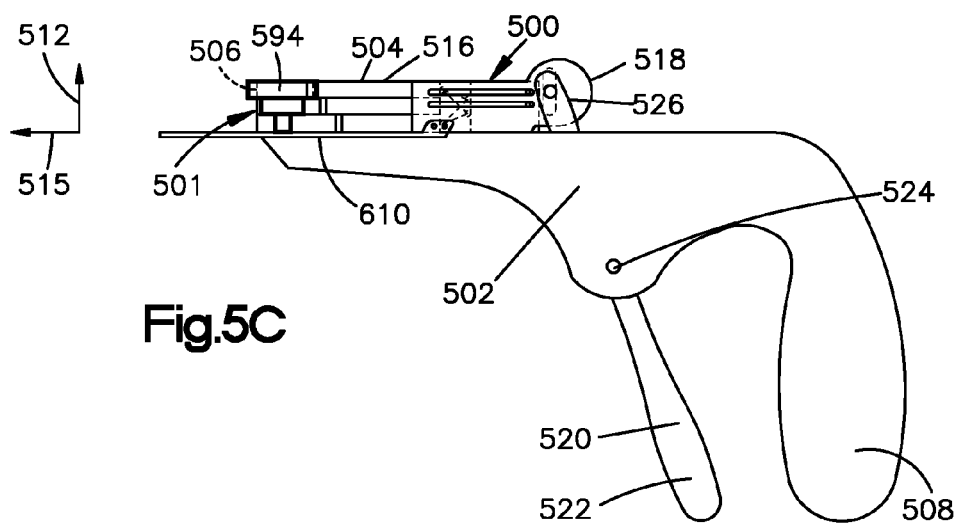
FIG. 5C is a side view of the bending tool of FIG. 5A, showing the first and second jaws in the second or closed position and the rollers in a second position.
Figure 5F:
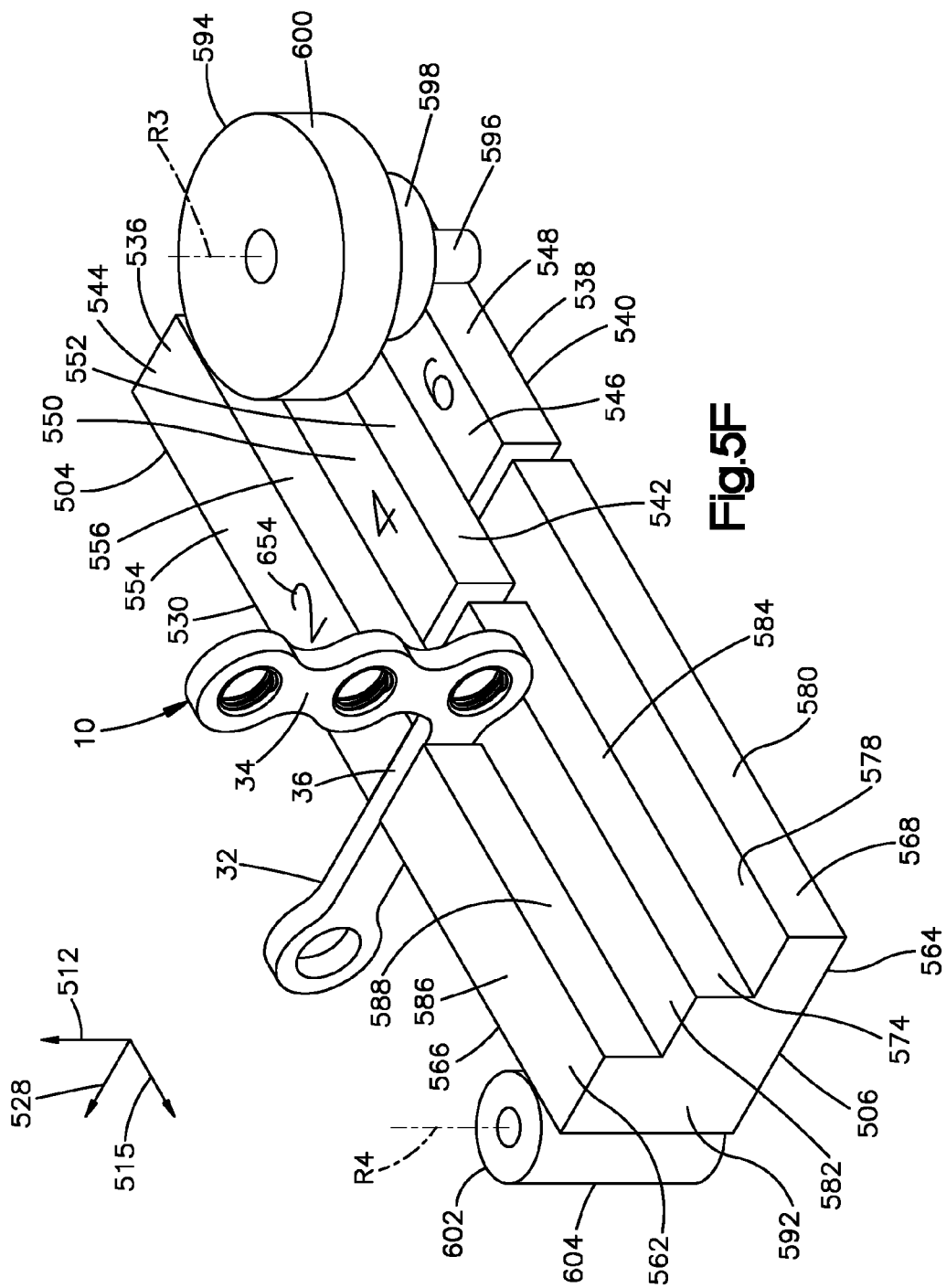
FIG. 5F is a perspective view of the bending mechanism of the bending tool shown in FIG. 5A, illustrating an orthopedic implant disposed in a gap between the first and second jaws.

The bending tool 500 includes the bending mechanism 501 is configured to bend the orthopedic implant 10 or any other suitable apparatus or device. The bending mechanism 501 includes a first jaw 504 and a second jaw 506 that are supported by tool support member 510. The tool support member 510 may support at least a portion of the first jaw 504 and the entire second jaw 506. For instance, the tool support member 510 may support the entire second jaw 506 and apportion of the first jaw 504. The first jaw 504 and the second jaw 506 are movable relative to one another between a first or open position (FIG. 5A) and a second or closed position (FIGS. 5B and 5C). In the depicted embodiment, only the first jaw 504 can move relative to the second jaw 506, while the second jaw 506 remains stationary relative to the tool body 502. However, it envisioned that only the second jaw 506 is capable of moving while the first jaw 504 remains stationary relative to the tool body 502. Further still, both the first jaw 504 and the second jaw 506 may be able to move relative to each other. Regardless of how the first jaw 504 and the second jaw 506 move with respect to each other, the first jaw 504 and the second jaw 506 collectively define an implant receiving gap 514 at least when the first jaw 504 and the second jaw 506 are in the open position. The implant receiving gap 514 is defined between the first jaw 506 and the second jaw 506 and is configured and sized to receive the orthopedic implant 10.

The first jaw 504 may include an engagement portion 516 and a coupling portion 518 that is spaced from the engagement portion 516 along the longitudinal direction 515. The engagement portion 516 is configured to engage the orthopedic implant 10 that is disposed in the implant receiving gap 514 so as to bend the orthopedic implant 10 when the second jaw 504 moves from the open position toward the closed position. The coupling portion 518 can be coupled to an actuator 520 that is configured to urge the first jaw 504 from the first position to the second position. The actuator 520 can be configured as a trigger 522 and is coupled to the coupling portion 518. A fastener 526, such as a pin or a screw, can couple the actuator 520 with the coupling portion 518 of the second jaw 504. In the depicted embodiment, the actuator 520 can also be movably coupled to the tool body 502. For example, a pivot member 524, such as a pivot pin, can pivotally couple the actuator 520 to the tool body 502, thereby allowing the actuator 520 to pivot about the pivot member 524 between a first position (FIGS. 5A and 5B) and a second position (FIG. 5C). Hence, the actuator 520 can be pivotally couple to the tool body 502. As such, the actuator 520 can pivot relative to the tool body 502 between a non-actuated position and actuated position. The bending tool 500 may include a basing member, such as a spring, to bias the actuator 250 toward the first position. The biasing member may, for example, be a coil spring disposed about the pivot member 524. In operation, the moving the actuator 520 from the first position toward the second position causes the first jaw 504 to move from the open position toward the closed position. Conversely, moving the actuator 520 from the second position toward the first position causes the first jaw 504 to move from the closed position toward the open position. Therefore, the actuator 250 can be configured to urge movement of the first jaw 504 between the open position and the closed position.

The first jaw 504 may have a stepped shape. For example, the first jaw 504 may be substantially shaped as stairs. The first jaw 504 defines a top surface 536 and a bottom surface 538 opposite the top surface 536. The top surface 536 can be spaced from the bottom surface 538 along the transverse direction 512. The top surface 536, the bottom surface 538, or both may be substantially planar. For example, the top surface 536, the bottom surface 538, or both may be substantially flat and may define a plane that extends along the longitudinal direction 515 and a lateral direction 528. The lateral direction 528 may be substantially perpendicular to the longitudinal direction 515 and the transverse direction 512. Moreover, the first jaw 504 includes a first side 530 and a second side 532 that is spaced from the first side along the lateral direction 528. The first side 530 may define a substantially planar first side surface 534. Specifically, the first side surface 534 may be substantially flat and may define a plane that extends along the longitudinal direction 515 and the transverse direction 512.

The second side 532 may include one or more stepped portions that are spaced from one another along the lateral direction 528 and the transverse direction 512. For example, in the depicted embodiment, the second side 532 may include a first stepped portion 540, a second stepped portion 542, and a third stepped portion 544 that are spaced from one another along the transverse direction 512 and the lateral direction 528. The first stepped portion 540 may be at least partially defined by a first top wall 546 and a first lateral wall 548 that may be oriented substantially orthogonal to the first top wall 546. The first top wall 546 may be substantially planar and may define a plane that extends along the longitudinal direction 515 and the lateral direction 528. The first lateral wall 548 may be substantially planar and may define a plane that extends along the longitudinal direction 515 and the transverse direction 512. The second stepped portion 524 may be at least partially defined by a second top wall 550 and a second lateral wall 552 that may be substantially orthogonal to the second top wall 550. The second top wall 550 may be substantially planar and may define a plane that extends along the longitudinal direction 515 and the lateral direction 528. The second lateral wall 552 may be substantially planar and may define a plane that extends substantially along the longitudinal direction 515 and the transverse direction 512. The third stepped portion 544 may also be at least partially defined by a third top wall 554 and a third lateral wall 556 that may be substantially orthogonal to the third top wall 554. The third top wall 554 may be substantially planar and may define a plane that extends along the longitudinal direction 515 and the lateral direction 528. The third lateral wall 556 may be substantially planar and may define a plane that extends along the longitudinal direction 515 and the transverse direction 512. The second stepped portion 542 may be disposed between the first stepped portion 540 and the third stepped portion 544. Each of the stepped portions 540, 542, 544 may include a marking. These markings are indicative of the offset distance that the orthopedic implant 10 would be bent if the orthopedic implant 10 is placed in the stepped portion with that marking. Although the drawings show three stepped portions, the first jaw 504 may alternatively include more or fewer stepped portions.

The first jaw 504 further defines a first inner engagement surface 558 and a first outer surface 560 that is opposite the first engagement surface 558. The first inner engagement surface 558 can be spaced from the first outer surface 560 along the longitudinal direction 515. While the first outer surface 560 may have a substantially planar configuration, the first inner engagement surface 558 may have a stepped configuration or shape due to the different lengths of the stepped portions 540, 542, 544. In the depicted embodiment, the first stepped portion 540 defines a first length L1 that extends from the first outer surface 560 to the first inner engagement surface 558 along the longitudinal direction 515. The second stepped portion 542 defines a second length L2 that extends from the first outer surface 560 to the first inner engagement surface 558 along the longitudinal direction 515. The third stepped portion 544 defines a third length L3 that extends from the first outer surface 560 to the first inner engagement surface 558 along the longitudinal direction 515. The third length L3 may be greater than the second length L2 and the first length L1. The second length L2 may be greater than the first length L1.

The second jaw 506 may be coupled to the tool support member 510 such that a position of the second jaw 506 is fixed relative to the tool body 502. In the depicted embodiment, the second jaw 506 may have a stepped configuration. For example, the second jaw 506 may be substantially shaped as stairs. The second jaw 506 defines a top surface 562 and a bottom surface 564 opposite the top surface 562. The top surface 562 may be spaced from the bottom surface 564 along the transverse direction 512. The bottom surface 562, the top surface 562, or both may be substantially planar. For instance, the bottom surface 562, the top surface 562, or both may be substantially flat and may define a plane that extends along the longitudinal direction 515 and the lateral direction 528. The second jaw further includes a first side 566 and a second side 568 opposite to the first side 566. The second side 568 may be spaced from the first side 566 along the lateral direction 528. The first side 566 may define a substantially planar side surface 570. Specifically, the side surface 570 may be substantially flat and may define a plane that extends along the longitudinal direction 515 and the transverse direction 512.

The second side 568 may include one or more stepped portions that are spaced from one another along the transverse direction 512 and the lateral direction 528. For example, in the depicted embodiment, the second side 568 may include a first stepped portion 572, a second stepped portion 574, and a third stepped portion 576 that are spaced from one another along the transverse direction 512 and the lateral direction 528. The first stepped portion 572 may be at least partially defined by a first top wall 578 and a first lateral wall 580 that may be oriented substantially orthogonal to the first top wall 578. The first top wall 578 may be substantially planar and may define a plane that extends along the longitudinal direction 515 and the lateral direction 528. The first lateral wall 580 may be substantially planar and may define a plane that extends along the longitudinal direction 515 and the transverse direction 512. The second stepped portion 574 may be at least partially defined by a second top wall 582 and a second lateral wall 584 that may be substantially orthogonal to the second top wall 582. The second top wall 582 may be substantially planar and may define a plane that extends substantially along the longitudinal direction 515 and the lateral direction 528. The second lateral wall 584 may be substantially planar and may define a plane that extends substantially along the longitudinal direction 515 and the transverse direction 512. The third stepped portion 576 may be at least partially defined by a third top wall 586 and a third lateral wall 588 that may be substantially orthogonal to the third top wall 586. The third top wall 586 may be substantially planar and may define a plane that extends along the longitudinal direction 515 and the lateral direction 528. The third lateral wall 588 may be substantially planar and may define a plane that extends along the longitudinal direction 515 and the transverse direction 512. Although the drawings that the second jaw 506 has three stepped portions, the second jaw 506 may alternatively include more or fewer stepped portions.

The second jaw 506 further defines a second inner engagement surface 590 and a second outer surface 592 that is opposite the second engagement surface 590. The second engagement inner surface 590 can be spaced from the second outer surface 592 along the longitudinal direction 515. The second outer surface 592 may have a substantially planar configuration, and the second inner engagement surface 590 may have stepped configuration or shape due to the different lengths of the stepped portions 572, 574, and 576. In the depicted embodiment, the first stepped portion 572 defines a first length L6 that extends from the second outer surface 592 to the second inner engagement surface 590 along the longitudinal direction 515. The second stepped portion 574 defines a second length L5 that extends from the second outer surface 592 to the second inner engagement surface 590 along the longitudinal direction 515. The third stepped portion 576 defines a third length L4 that extends from the second outer surface 592 to the second inner engagement surface 590 along the longitudinal direction 515. The first length L6 may be greater than the second length L5 and the third length L4. The second length L5 may greater than the first length L4.

In addition to the first jaw 504 and the second jaw 506, the bending mechanism 501 includes a first roller 594 that is movably coupled to the first jaw 504 and the second jaw 506. Specifically, the first roller 594 is configured to move along the second side 532 of the first jaw 506 and along the second side 568 of the second jaw 506 in the longitudinal direction 515. The first roller 594 may have a substantially stepped configuration. For example, in the depicted embodiment, the first roller 594 may include a first roller portion 596, a second roller portion 598, and a third roller portion 600 that are spaced from one another along the transverse direction 512. It is contemplated that first roller 594 may include fewer or more than three roller portions. Regardless of the number of roller portions, the first roller 594 is configured to rotate along a first rotation axis R3. Consequently, the first roller portion 596, the second roller portion 598, and the third roller portion 600 can rotate about the first rotation axis R3.

The first roller portion 596 may be shaped as a disk or a cylinder and defines a first roller cross-sectional dimension D1 such as a diameter The first roller cross-sectional dimension D1 may be a diameter. The second roller portion 598 may be shaped as a disk or a cylinder and defines a second roller cross-sectional dimension D2 such as a diameter. The second cross-sectional dimension D2 may be a diameter. The third roller portion 600 may be shaped as a disk or a cylinder and defines a third roller cross-sectional dimension D3 such as a diameter. The third roller cross-sectional dimension D3 may be a diameter. Further, the third roller cross-sectional dimension D3 may be greater than the second roller cross-sectional dimension D2 and the first roller cross-sectional dimension D1. The second roller cross-sectional dimension D2 may be greater than the first roller cross-sectional dimension D1. The different cross-sectional dimensions of the first roller 594 allows the first roller 594 to travel along the stepped sides of the first jaw 504 and the second jaw 506. That is, the first roller 594 is configured to move along the second side 532 of the first jaw 504 and the second side 568 of the second jaw 506. Specifically, the first roller portion 596 is configured and sized to roller along the first lateral wall 548 and the first lateral wall 580 of the first jaw 504 and the second jaw 506, respectively, in the longitudinal direction 515. The second roller portion 598 is configured and sized to roll along the second lateral wall 552 and the second lateral wall 584 in the longitudinal direction 515. The third roller portion 600 is configured and sized to roll along the third lateral wall 556 and the third lateral wall 588 in the longitudinal direction 515. In operation, the first roller 594 can rotate about the first rotation axis R3 while it advances along the first jaw 504 and the second jaw 506 in the longitudinal direction 515 in order to bend a portion of the orthopedic implant 10.

The bending mechanism 501 includes a second roller 602 that is movably coupled to the first jaw 504 and the second jaw 506. In particular, the second roller 602 can be configured to rotate about an rotation axis R4 and can move along the first side 530 of the first jaw 506 and the first side 566 of the second jaw 506 in the longitudinal direction 515. The first roller 602 may define a roller body 604, which may have a substantially cylindrical shape. Thus, the roller body 604 may define a substantially circular cross-section. In operation, the roller 60 can move along the first jaw 504 and the second jaw 506 in the longitudinal direction 515 while rotating about the rotation axis R4 in order to bend a portion of the orthopedic implant 10.

Figure 5J:
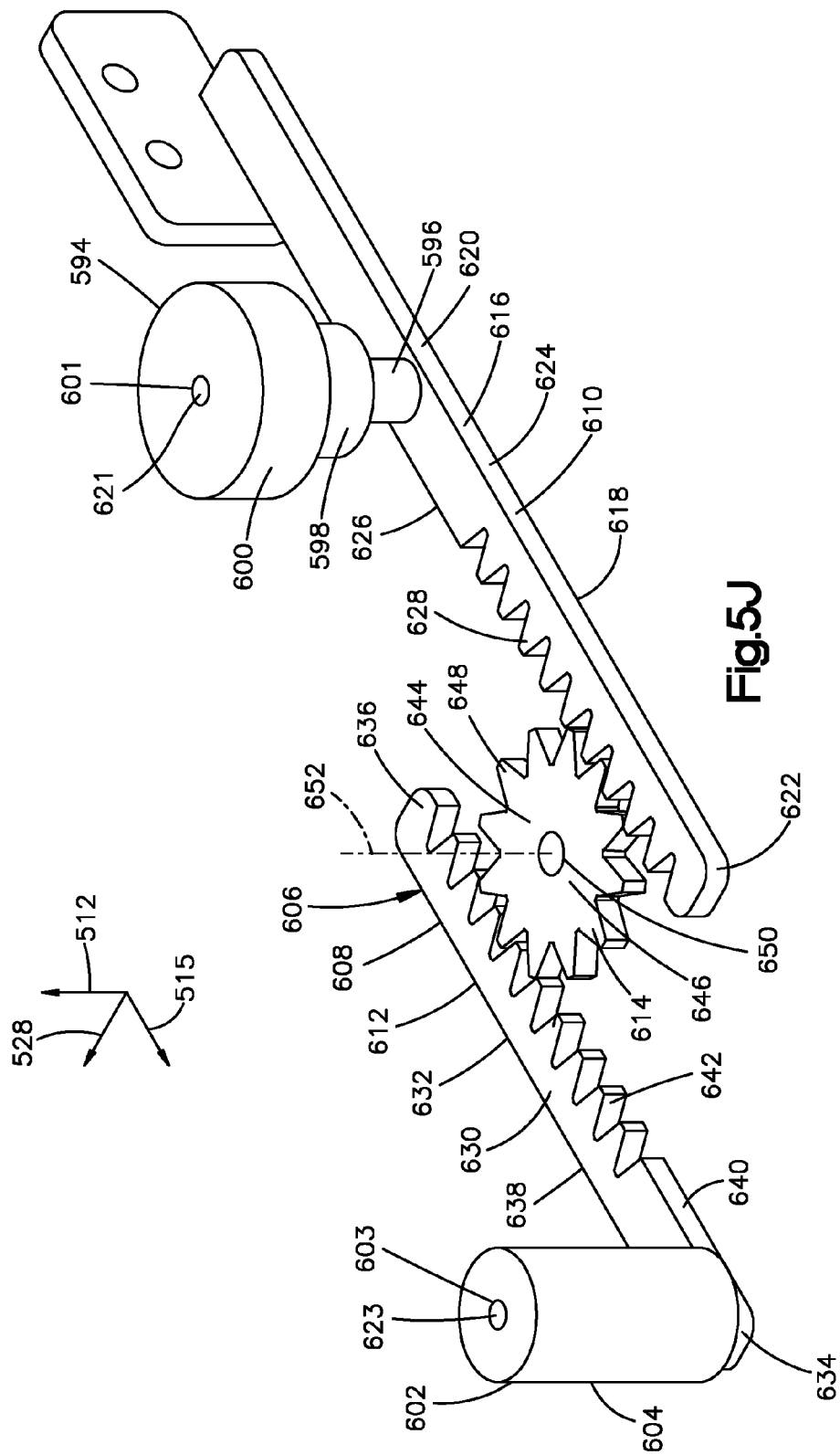
FIG. 5J is a perspective view of an actuation mechanism configured to move the rollers shown in FIGS. 5H and 5I between the first position and the second position.

With reference to FIG. 5J, the bending mechanism 501 further includes an actuation mechanism 606 configured to drive to first roller 594 and the second roller 602 along the first jaw 504 and the second jaw 506 in the longitudinal direction 515. In the depicted embodiment, the actuation mechanism 606 can be configured as a rack and pinion mechanism 608 and may include a first drive member 610, a second drive member 612, and a third drive member 614. The third drive member 614 is mechanically coupled between the first drive member 610 and the second drive member 612. In operation, rotating third drive member 614 causes the first drive member 610 and the second drive member 612 to move in opposite directions. For example, the first drive member 610 and the second drive member 612 can translate upon rotation of the third drive member 614.

The first drive member 610 may be configured as a first rack 616 and is coupled to the first roller 594. Therefore, moving the first drive member 610 in the longitudinal direction 515 causes the first roller 594 to move in the longitudinal direction 515 as well. The first drive member 610 may include a first drive body 618 that is elongate along the longitudinal direction 515. The first drive body 618 defines a first end 620 and a second end 622 that is opposite the first end 620. The second end 622 can be spaced from the first end 620 along the longitudinal direction 515. The first roller 594 may be coupled at the first end 620 of the first drive body 618. In particular, the first roller portion 596 of the first roller 594 may be coupled at the first end 620 of the first drive body 618 through, for example, a first roller coupler 621. The first roller coupler 621 may be configured as a rod and is connected to the first drive body 618. For example, the first roller coupler 621 may be elongate along the transverse direction 512 and may be connected at the first end 620 of the first drive body 618. The first roller 594 may define a first roller opening 601 that is configured and sized to receive the first roller coupler 621, thereby allowing the first roller 594 to rotate about the first roller coupler 621. The first roller opening 601 may extends through the first roller portion 596, the second roller portion 598, and the third roller portion 600 along the transverse direction 512. The first drive body 618 further defines a first side 624 and a second side 626 that is opposite the first side 624. The second side 626 may be spaced from the first side 624 along the lateral direction 528. The first drive member 610 may further include a plurality of teeth 628 that protrude from the second side 626 of the first drive body 618 along the lateral direction 528. The teeth 628 may be spaced from one another along the longitudinal direction 515. In the depicted embodiment, the teeth 628 are located closer to the second end 622 than the first end 620. The teeth 628 may protrude from the first drive body 618 in a toward the second drive member 612 and the third drive member 614.

As discussed above, the actuation mechanism 606 includes the second drive member 612 that is operatively coupled to the first drive member 610 via the third drive member 614. The second drive member 612 may be configured as a second rack 630 and is coupled to the second roller 602. Therefore, moving the second drive member 612 in the longitudinal direction 515 causes the second roller 602 to move in the longitudinal direction 515 as well. The second drive member 612 may include a second drive body 632 that is elongate along the longitudinal direction 515. The second drive body 632 defines a first end 634 and a second end 636 that opposite the first end 634. The second end 636 may be spaced from the first end 634 along the longitudinal direction 515. The second roller 602 may be coupled at the first end 634 of the second drive body 632 through, for example, a second roller coupler 623. The second roller coupler 623 may be configured as a rod and is connected to the second drive body 632. For instance, the second roller coupler 623 may be elongate along the transverse direction 512 and may be connected at the first end 634 of the second drive body 632. The second roller 602 may define a second roller opening 603 that is configured and sized to receive the second roller coupler 623, thereby allowing the second roller 602 to rotate about the second roller coupler 623. The second roller opening 603 may extend through the roller body 604 along the transverse direction 512. The second drive body further defines a first side 638 and a second side 640 that is opposite from the first side 638. The second side 640 may be spaced from the first side 638 along the lateral direction 528. The second drive member 612 may further include a plurality of teeth 642 that protrude from the second side 640 of the second drive body 632 along the lateral direction 528. The teeth 642 may be spaced from one another along the longitudinal direction 515. In the depicted embodiment, the teeth 642 may be located closer to the second end 636 than to the first end 634. The teeth 642 may protrude from the second drive body 632 in a direction toward the first drive member 610 and the third drive member 614.

The third drive member 614 can be configured as a pinion 644 or a gear, which can be driven by one of the first and second drive members 610 and 612 which moves in a first longitudinal direction, so as to cause the other of the first and second drive members 610 and 612 to reciprocally move in a second longitudinal direction that is opposite the first longitudinal direction. In the depicted embodiment, the third drive member 614 includes a third drive body 646 and a plurality of teeth 648 that protrude radially outwardly from the third drive body 646. The third drive body 646 may be substantially shaped as a disk and the teeth 648 include may be disposed around the perimeter of the third drive body 646. For example, the teeth 648 may be spaced from one another about the circumference of the third drive body 646. The teeth 648 are configured to mesh with the teeth 628 of the first drive member 610 and the teeth 642 of the second drive member 612. In addition to the teeth 648, the third drive member 614 may define a central bore 650 that is configured and sized to receive driving member, such as a shaft or a rod. The central bore 650 defines a rotation axis 652 that may extend along the driving member in the transverse direction 512. The driving member may be coupled to an electric motor, a pneumatic motor or any other source of mechanical energy that is capable of rotating the driving member in order to rotate the third drive member 614 about the rotation axis 652. The third drive member 614 is configured to rotate about the rotation axis 652. In operation, the rotation of the third drive member 614 about the rotation axis 652 causes the first drive member 610 and the second drive member 612 to move longitudinally in opposite directions. As the first drive member 610 and the second drive member 612 move longitudinally, the first roller 594 and the second roller 602 also move longitudinally in opposite directions.

With reference to FIGS. 5F-5I, as discussed above, the first jaw 504 and the second jaw 506 collectively define disposed in the implant receiving gap 514. Specifically, the implant receiving gap 514 is at least partially defined by the first inner engagement surface 558 and the second inner engagement surface 590. In operation, the orthopedic implant 10 can be disposed in the implant receiving gap 514 between the first jaw 504 and the second jaw 506. The second jaw 506 can then be moved from the open position (FIG. 5A) toward the closed position (FIG. 5B) by, for instance, actuating the trigger 522 in order to hold the orthopedic implant 10 between the first jaw 504 and the second jaw 506. In this embodiment, the orthopedic implant 10 includes a first implant portion 32, a second implant portion 34, a third implant portion 36 that is disposed between the first implant portion 32 and the second implant portion 34. When the first jaw 504 and the second jaw 506 hold the orthopedic implant 10, the first inner engagement surface 558 and the second inner engagement surface 590 contact the third implant portion 36, while the first implant portion 32 and the second implant portion 34 are located outside the implant receiving gap 514. The third implant portion 36 may be disposed between 1) the first stepped portion 540 of the first jaw 504 and the first stepped portion 572 of the second jaw 506; 2) the second stepped portion 542 of the first jaw 504 and the second stepped portion 574 of the second jaw 506; or 3) the third stepped portion 544 of the first jaw 504 and the third stepped portion 576 of the second jaw 506.

The bending tool 500 is configured to bend the orthopedic implant 10 such that the first implant portion 32 is offset from the second implant portion 34 by a predetermined offset distance O. The offset distance O is the distance from the first implant portion 32 to the second implant portion 34 along the lateral direction 528 after the orthopedic implant 10 has been bent by the bending tool 500 as shown in FIG. 5I. In the depicted embodiment, the offset distance O can be at least partially defined by a distance from the first side 530 of the first jaw 504 to the lateral wall of one of the stepped portions of the first jaw 504 in the lateral direction 528. Also, the offset distance O can be at least partially defined by the distance from the first side 566 to one of the lateral walls of the stepped portions of the second jaw 506 in the lateral direction 528. The distance from the first side of a jaw to one of the lateral walls of the stepped portions of that same jaw can be referred to as the bending distance. The bending tool 500 may define a plurality of bending distances. For instance, a first bending distance B1 may be defined as the distance from the first side 530 to the first lateral wall 548 of the first stepped portion 540 in the lateral direction 528. The first bending distance B1 may also be the distance from the first side 566 to the first lateral wall 580 of the first stepped portion 580 along the lateral direction 528. A second bending distance B2 may be the distance from the first side 530 to the second lateral wall 552 along the lateral direction 528. The second bending distance B2 may also be the distance from the first side 566 to the second lateral wall 584 along the lateral direction 528. A third bending distance B3 may be the distance from the first side 530 to the third lateral wall 556 along the lateral direction 528. The third bending distance B3 may also be the distance from the first side 566 to the third lateral wall 588 along the lateral direction 528. The offset distance O may be substantially similar or identical to the first bending distance B1, the second bending distance B2 or the third bending distance B3 depending on where the third implant portion 36 is located relative to the stepped portions when the orthopedic implant 10 is being bent. For example, the offset distance O may be substantially similar or identical to the first bending distance B1 if the third implant portion 36 is disposed between the first stepped portion 540 of the first jaw 504 and the first stepped portion 572 of the second jaw 506. The offset distance O may be substantially similar or identical to the second bending distance B2 if the third implant portion 36 is disposed between the second stepped portion 542 of the first jaw 504 and the second stepped portion 574 of the second jaw 506. The offset distance O may be substantially similar or identical to the third bending distance B3 if the third implant portion 36 is disposed between the third stepped portion 544 of the first jaw 504 and the third stepped portion 576 of the second jaw 506. Accordingly, either the first jaw 50 or the second jaw 506 may include markings 654 in each stepped portion to assist the user in identifying the bending distance.

Once the third implant portion 36 has been disposed at the desired location relative to the stepped portion and the second jaw 506 has been moved toward the closed position, the first roller 594 and the second roller 602 can be moved along the first jaw 504 and the second jaw 506 to bend the orthopedic implant 10. Specifically, third drive member 614 is rotated about the rotation axis 652. As a result, the first drive member 510 urges the first roller 594 to move relative to the first jaw 504 and the second jaw 506 between a first position (FIG. 5H) and a second position (FIG. 5I) in a first direction 656. The first roller 594 may rotate about the rotation axis R3 as it moves along the first jaw 504 and the second jaw 504. Upon rotation of the third drive member 614, the second drive member 612 urges the second roller 602 to move relative to the first jaw 504 and the second jaw 506 between a first position (FIG. H) and a second position (FIG. 5I) in a second direction 658. The second direction 658 may be opposite to the first direction 656. The second roller 602 may rotate about the rotation axis R4 as it moves along the first jaw 504 and the second jaw 506. During rotation of the third drive member 614, the first roller 594 and the second roller 602 may be simultaneously and at the same speed. However, it is envisioned, that the first roller 594 may move independently of the second roller 602.

While moving from the first position (FIG. 5H) to the second position (FIG. 5I), the first roller 594 contacts the second implant portion 34, thereby changing the orientation of the second implant portion 34 relative to the third implant portion 36. For example, the second implant portion 34 may initially define a plane that extends along the transverse direction 512 and the lateral direction 528. After the first roller 594 passes over the second implant portion 34, the second implant portion 34 may define a plane that extends along the longitudinal direction 515 and the transverse direction 512. While moving from the first position (FIG. 5H) to the second position (FIG. 5I), the second roller 602 contacts the first implant portion 32, thereby changing the orientation of the first implant portion 32 relative to the third implant portion 36. For instance, the first implant portion 32 may initially define a plane that extends along the lateral direction 528 and the transverse direction 512. After the second roller 602 passes over the first implant portion 32, the first implant portion 32 may define a plane that extends along the longitudinal direction 515 and the transverse direction 512. At the end of the bending process, the first implant portion 32 is offset relative to the second implant portion 34 a predetermine offset distance O. As discussed above, the offset distance O may be substantially similar to one of the bending distance B1, B2, or B3.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A bending tool that is configured to bend an orthopedic implant that includes a first implant portion and a second implant portion, the bending tool comprising:
   a first jaw;
   a second jaw spaced from the first jaw along a longitudinal direction, the second jaw being movably coupled to the first jaw such that the first and second jaws are movable with respect to each other along the longitudinal direction, wherein a gap is defined between the first and second jaws, the second jaw includes a first side and a second side that is spaced from the first side along a lateral direction that is substantially perpendicular to the longitudinal direction, the first side defines a first side surface, the second side defines a first lateral wall and a second lateral wall that is spaced from the first lateral wall along the lateral direction and a transverse direction that is substantially perpendicular to the longitudinal and lateral directions, a first distance is defined from the first side surface to the first lateral wall along the lateral direction, and a second distance is defined from the first side surface to the second lateral wall along the lateral direction; and
   a roller that is configured to move along the first and second lateral walls along the longitudinal direction so as to apply a force to a portion of the orthopedic implant that is disposed outside the gap, thereby bending the orthopedic implant such that the first implant portion is offset relative to the second implant portion by an offset distance, the offset distance is substantially defined by the first distance when a portion of the orthopedic implant that is disposed in the gap is substantially aligned with the first lateral wall along the transverse direction or by the second distance when the portion of the orthopedic implant that is disposed in the gap is substantially aligned with the second lateral wall along the transverse direction.

2. The bending tool according to claim 1, wherein the roller includes a first roller portion and a second roller portion that is coupled to and spaced from the first roller portion, the first roller portion defines a first cross-sectional dimension, the second roller portion defines a second cross-sectional dimension, and the first cross-sectional dimension is different from the second cross-sectional dimension.

3. The bending tool according to claim 2, wherein the first roller portion is configured to move along the first lateral wall so as to apply the force to the portion of the orthopedic implant that is disposed outside the gap.

4. The bending tool according to claim 1, wherein the roller is a first roller, and the bending tool further comprises a second roller that is configured to move along the first side surface so as to apply a force to another portion of the orthopedic implant that is disposed outside the gap.

5. The bending tool according to claim 4, further comprising an actuation mechanism that is configured to drive to first roller and the second roller simultaneously along the first jaw and the second jaw along the longitudinal direction.

6. The bending tool according to claim 5, wherein the actuation mechanism includes a first drive member that is coupled to the first roller, a second drive member that is coupled to the second roller, and a third drive member connected between the first and second drive members, and rotation of the third drive member about a rotation axis causes the first and second drive members to move simultaneously in opposite directions.

7. The bending tool according to claim 4, wherein the first side surface is substantially planar, and the second roller defines a substantially constant cross-section.

8. The bending tool according to claim 1, wherein the first and second jaws are configured to move relative to each other to apply a force to the portion of the orthopedic implant that is disposed in the gap, thereby holding the orthopedic implant with respect to the first and second jaws.

9. The bending tool according to claim 8, wherein the second jaw is configured to move relative to the first jaw while the first jaw remains stationary.

10. The bending tool according to claim 9, further comprising a tool body and an actuator movably coupled to the tool body, wherein the actuator is coupled to the second jaw such that moving the actuator relative to the tool body causes the second jaw to move relative to the first jaw.

11. The bending tool according to claim 1, wherein the second jaw defines a plurality of stepped portions offset from each other along the transverse direction.

12. A method of bending an orthopedic implant with a bending tool, the method comprising:
    positioning a portion of the orthopedic implant in an implant receiving gap that is defined between first and second jaws supported by a tool body of the bending tool, the first jaw being spaced from the second jaw along a longitudinal direction, the first jaw including at least one wall having a first side and a second side spaced from the first side by a first distance along a lateral direction that is substantially perpendicular to the longitudinal direction;

moving the first and second jaws relative to each other along the longitudinal direction from an open position to a closed position, such that the implant receiving gap defines 1) a first distance along the longitudinal direction in the open position, and 2) a second distance along the longitudinal direction in the closed position, wherein the second distance is less than the first distance along the longitudinal direction; and moving a roller onto the orthopedic implant so as to urge the orthopedic implant against the second side, thereby causing a first portion of the orthopedic implant to be offset from a second portion of the orthopedic implant by an offset distance that is equal to or greater than the first distance along the lateral direction.

13. The method of claim 12, wherein the roller is a first roller carried by the tool body, the method further comprises moving a second roller along the first side, and the second roller is carried by the tool body.

14. The method of claim 12, wherein the at least one wall comprises a first wall, a second wall, and a third wall, wherein each of the first, second and third walls defines respective first and second sides and respective bending distances defined from the respective first side to the respective second side of the first, second, and third walls.

15. The method of claim 14, wherein the first roller includes a first roller portion, a second roller portion, and a third roller portion that are spaced from one another along a transverse direction that is substantially perpendicular to the lateral and longitudinal directions, wherein the first roller portion defines a first cross-sectional dimension, the second roller portion defines a second cross-sectional dimension that is greater than the first cross-sectional dimension, and the third roller portion defines a third cross-sectional dimension that is greater than the first and second cross-sectional dimensions.

16. The method of claim 15, wherein moving the first roller further comprises rolling the first roller portion along the second side of the first wall;

rolling the second roller portion along the second side of the second wall; and rolling the third roller portion along the second side of the third wall.

17. The method of claim 12, wherein the first jaw further defines a plurality of stepped portions offset from each other along a transverse direction that is perpendicular to the longitudinal and lateral directions.

18. A bending tool that is configured to bend an orthopedic implant that includes a first implant portion and a second implant portion, the bending tool comprising:

a first jaw;

a second jaw spaced from the first jaw along a longitudinal direction, the second jaw being movably coupled to the first jaw such that the first and second jaws are movable with respect to each other along the longitudinal direction, and a gap is defined between the first and second jaws, the first jaw defining a plurality of stepped portions, wherein each stepped portion defines 1) a first side, 2) a second side spaced from the first side by a bending distance along a lateral direction that is perpendicular to the longitudinal direction, and 3) a top side that extends between the first and second sides; and a roller configured to move along the plurality of stepped portions along the longitudinal direction, wherein movement of the roller relative to the plurality of stepped portions biases the second implant portion against a second side of one of the plurality of stepped portions, such that the first and second implant portions are offset by an offset distance that is defined by the bending distance of an associated one of the plurality of stepped portions.

19. The bending tool according to claim 18, wherein the plurality of stepped portions includes first, second, and third stepped portions defining first, second, and third bending distances, respectively, such that the first bending distance is greater than the second and third bending distances, and the second bending distance is greater than the third bending distance.

20. The bending tool according to claim 19, wherein the first, second, and third stepped portions are offset from each other along a transverse direction that is perpendicular to the lateral and longitudinal directions.

* * * * *